US 9,458,226 B2

(12) United States Patent
Wrammert et al.

(10) Patent No.: US 9,458,226 B2
(45) Date of Patent: Oct. 4, 2016

(54) RECOMBINANT ANTIBODIES AGAINST H1N1 INFLUENZA

(75) Inventors: Jens Wrammert, Decatur, GA (US); Rafi Ahmed, Atlanta, GA (US); Patrick Wilson, Chicago, IL (US)

(73) Assignees: Emory University, Atlanta, GA (US); The University of Chicago, Chicago, IL (US)

( * ) Notice: Subject to any disclaimer, the term of this patent is extended or adjusted under 35 U.S.C. 154(b) by 196 days.

(21) Appl. No.: 13/500,879

(22) PCT Filed: Oct. 12, 2010

(86) PCT No.: PCT/US2010/052274
§ 371 (c)(1),
(2), (4) Date: Jun. 26, 2012

(87) PCT Pub. No.: WO2011/044570
PCT Pub. Date: Apr. 14, 2011

(65) Prior Publication Data
US 2012/0282273 A1    Nov. 8, 2012

Related U.S. Application Data

(60) Provisional application No. 61/250,479, filed on Oct. 9, 2009, provisional application No. 61/260,650, filed on Nov. 12, 2009.

(51) Int. Cl.
*C07K 16/00* (2006.01)
*A61P 31/16* (2006.01)
*A61K 39/42* (2006.01)
*C07K 16/10* (2006.01)
*A61K 39/00* (2006.01)

(52) U.S. Cl.
CPC ..... *C07K 16/1018* (2013.01); *A61K 2039/505* (2013.01); *C07K 2317/21* (2013.01); *C07K 2317/76* (2013.01)

(58) Field of Classification Search
CPC .......................... A61K 39/145; C07K 14/005
See application file for complete search history.

(56) References Cited

U.S. PATENT DOCUMENTS

| | | | |
|---|---|---|---|
| 5,684,146 | A | 11/1997 | Okuno et al. |
| 2005/0684146 | | 11/1997 | Yoshinobu |
| 2002/0054882 | A1 | 5/2002 | Okuno et al. |
| 2014/0348851 | A1 | 11/2014 | Ahmed et al. |

FOREIGN PATENT DOCUMENTS

| | | |
|---|---|---|
| EP | 10822829.7 | 12/2010 |
| WO | WO 2008/028946 A2 | 3/2008 |
| WO | WO 2009/115972 A1 | 9/2009 |
| WO | WO 2011/044570 | 10/2010 |

OTHER PUBLICATIONS

Li et al. (PNAS, Jun. 2012, vol. 109, p. 9047-9052).*
O'Donnell et al., (Mbio May 2012, p. 1-10).*
Wrammert et al. (JEM, 2009, p. 181-193).*
Wilson, Nov. 2008, Gen Bank FJ475055, p. 1-3.*
International Search Report from the prior PCT Patent Application No. PCT/US2010/052274, 6 pages (mailed on Jun. 27, 2011).
Kubota-Koketsu et al., "Broad neutralizing human monoclonal antibodies against influenza virus from vaccinated healthy donors," Biochem. Biophys. Res. Comm. 387: 180-185 (Jul. 4, 2009).
Throsby et al., "Heterosubtypic neutralizing monoclonal antibodies cross-protective against H5N1 and H1N1 recovered from human IgM+ memory B cells," PLos One 3(12): e3942 (Dec. 16, 2008).
Warmmert et al., Rapid cloning of high affinity human monoclonal antibodies against influenza virus, Nature 453(7195): 667-671 (May 29, 2008).
Yoshida et al., "Cross-protective potential of a novel monoclonal antibody directed against antigenic site B of the hemagglutinin of influenza A viruses," PLos Pathog. 5(3): e1000350 (Mar. 20, 2008).
MMWR Dispatch 2009; 58:1-3. Available at: http:www.cdc.gov/mmwr/preview/mmwrhtml/mm58d0421a1.htm).
Ahmed, et al., 2007, Protective immunity and susceptibility to infectious diseases: lessons from the 1918 influenza pandemic. Nat Immunol, 8(11), 1188-1193.
Brockwell-Staats, et al., 2009, Diversity of Influenza Viruses in Swine and the Emergence of a Novel Human Pandemic Influenza A (HINI). Influenza Other Respi Viruses 3(5), 207-213.
Chiu, et al., 2013, "Cross-reactive humoral responses to influenza and their implications for a universal vaccine", Ann N Y Acad Sci, 1283:13-21.
Compans, R.W., 1974, "Hemagglutination-inhibition: rapid assay for neuraminic acid containing Viruses", J Virol 14(5), 1307-1309.
Dawood, et al., 2009, "Emergence of a novel swine-origin influenza A (RINI) virus in humans", N Engl J Med, 360 (25):2605-2615.
Garten, et al., 2009, "Antigenic and genetic characteristics of swine-origin 2009 A(HINI) influenza viruses circulating in humans", Science, 325(5937), I97-201.
Hancock, et al., 2009, "Cross-Reactive Antibody Responses to the 2009 Pandemic HINI Influenza Virus", N Engl J Med, 361(20): 1945-1952.
Kubota-Koketsu, et al., 2009, "Broad neutralizing human monoclonal antibodies against influenza virus from vaccinated healthy donors", Biochem Biophys Res Commun, 387(1): 180-185.
Li, et al., 2012, "Pandemic H1N1 influenza vaccine induces a recall response in humans that favors broadly cross-reactive memory B cells", Proc Natl Acad Sci U S A, 109(23):9047-9052.

(Continued)

*Primary Examiner* — Agnieszka Boesen
(74) *Attorney, Agent, or Firm* — Emory Patent Group

(57) ABSTRACT

Antibodies that bind with high affinity to swine H1N1 virus are described. In vivo experiments showed that one such antibody is able to fully protect mice challenged with a lethal dose of swine H1N1 virus. The antibody is also able to cure mice in a therapeutic setting when treated as late as up to 60 hours (2.5 days) after infection with swine H1N1 virus. Also described are recombinant forms of this antibody.

10 Claims, 6 Drawing Sheets

(56) References Cited

OTHER PUBLICATIONS

Nakajima, et al., 1983, "Identification of the binding sites to monoclonal antibodies on A/USSR/90/77 (HINI) hemagglutinin and their involvement in antigenic drift in HINI influenza viruses", Virology, 131(1): 116-127.

Nakaya, et al., 2011, "Systems biology of vaccination for seasonal influenza in humans", Nat Immunol, 12 (8):786-795.

Sheerar, et al., 1989, "Antigenic conservation of H1N1 swine influenza viruses", J Gen Virol, 70(12): 3297-3304.

Smith, et al., 2009, "Rapid generation of fully human monoclonal antibodies specific to a vaccinating antigen", Nat Protoc, 4(3):372-384.

Throsby, et al., 2008, "Heterosubtypic neutralizing monoclonal antibodies cross-protective against H5NI and HINI recovered from human IgM+ memory B cells", PLos One, 3(12): e3942.

Vareckova, et al., 2002, "Evaluation of the subtype specificity of monoclonal antibodies raised against HI and H3 subtypes of human influenza A virus hemagglutinins", J Clin Microbiol, 40(6): 2220-2223.

Wentworth et al, 1994, "An influenza A (HINI) virus, closely related to swine influenza virus, responsible for a fatal case of human influenza", J Virol, 68(4): 2051-2058.

Wrammert et al., 2008, "Rapid cloning of high-affinity human monoclonal antibodies against influenza virus", Nature, 453(7915):667-671.

Wrammert, et al., 2011, "Broadly cross-reactive antibodies dominate the human B cell response against 2009 pandemic HINI influenza virus infection", J Exp Med, 208(1): 181-193.

Yamashita, et al., 2010, "Highly conserved sequences for human neutralization epitope on hemagglutinin of influenza A viruses H3N2, HINI and H5NI: Implication for human monoclonal antibody recognition", Biochem Biophys Res Commun, 393(4): 614-618.

Yoshida, et al., 2008, "Cross-protective potential of a novel monoclonal antibody directed against antigenic site B of the hemagglutinin of influenza A viruses", PLos Pathog, 5(3), e1000350.

European Search Opinion, dated Sep. 8, 2013, for to European Patent Application 10822829.7 filed Dec. 10, 2010.

Supplementary Search Report, dated Sep. 8, 2013, for European Patent Application 10822829.7 filed Dec. 10, 2010.

International Search Report, dated Sep. 29, 2013 for international publication No. WO2011/044570 filed Oct. 12, 2012.

Supplemental information from Wrammert et al., 2008, "Rapid cloning of high-affinity human monoclonal antibodies against influenza virus", Nature, 453(7915):667-671.

Wilson, Gene Bank Accession No. FJ475055, Cloning vector AbVec-hIgG1, Antibody variable gene expression vector for human IgG1 heavy chain, 2008.

Brusco et al. "Variability of the immunoglobulin heavy chain constant region locus: a population study" Hum Genet, 1995; 95: 319-326.

Fett et al. "The Variability of Human 2-Chain Constant Regions and Some Relationships to V-Region Sequences" Immunochemistry, 1976; 13: 149-155.

Jefferis et al. "Human immunoglobulin allotypes" mAbs, 2009; 1(4): 1-7.

\* cited by examiner

Vaccines/Mix ($K_d = 6.1 \times 10E-11$)

- A/CA/04/2009 (SOIV-H1N1)
- Annual Cocktail[1]
- 2006/7 Vaccine[2]
- 2008/9 Vaccine[3]

Purified Virus

- A/CA/04/2009 (SOIV-H1N1)
- A/New Cal./20/99 (H1N1)
- A/Sol. Is./3/2006 (H1N1)
- A/WI/57/05 (H3N2)
- B/Mal./2506/04

Recombinant HA (rHA)

($K_d = 9.5 \times 10E-11$)

- rHA A/CA/04/2009 (SOIV-H1N1)
- rHA A/Bris./59/2007 (H1N1)
- rHA A/Bris./10/2007 (H3N2)
- rHA A/Indo./05/2005 (H5N1)

B.

Swine H1N1 rHA pulldown

C.

Swine H1N1 HAI activity

97% (30/31) of the mice lethally infected with pandemic swine H1N1 were rescued by EM4C04 treatment

RECOMBINANT ANTIBODIES AGAINST H1N1 INFLUENZA

CROSS REFERENCE TO RELATED APPLICATION

This application is the U.S. National Stage of PCT Application No. PCT/US2010/052274, filed Oct. 12, 2010, which was published in English under PCT Article 21(2), which claims the benefit of U.S. Provisional Application No. 61/260,650, filed on Nov. 12, 2009 and U.S. Provisional Application No. 61/250,479, filed on Oct. 9, 2009.

ACKNOWLEDGEMENT

This invention was made with government support under Grants AI057158, AI057266 and HHSN2662007000 awarded by the National Institutes of Health. The government has certain rights in the invention.

BACKGROUND

The swine H1N1 influenza virus is currently causing a world-wide pandemic associated with substantial morbidity and mortality[1-5]. This newly emergent strain is immunologically distinct from other influenza viruses including recent H1N1 strains[6] thus leaving a large population of the world highly susceptible to infection by this pandemic virus[7]. Although there is some B cell cross-reactivity with the seasonal influenza viruses the protective epitopes of the swine H1N1 virus appear to be quite distinct.

SUMMARY

Described herein are recombinant antibodies (e.g., human monoclonal antibodies) against the swine H1N1 influenza virus.

Described herein are antibodies derived from plasmablasts isolated from patients during (or shortly after) infection with the novel influenza virus. Among the antibodies described herein is an antibody that binds with particularly high affinity, is highly specific to swine H1N1 virus, and is able to mediate hemagglutination-inhibition at low concentrations. In vivo experiments showed that this antibody is able to fully protect mice challenged with a lethal dose of swine H1N1 virus. The antibody is also able to cure mice in a therapeutic setting when treated as late as up to 60 hours (2.5 days) after infection with swine H1N1 virus. Such antibodies have great potential as a human therapeutic or prophylactic agent against the novel swine H1N1 influenza.

In one aspect, the recombinant antibodies described herein include all or part of the amino acid sequence of SEQ ID NO:1 (light chain) and/or all or part of the amino acid sequence of SEQ ID NO:2 (heavy chain). Within the light chain, the variable domain includes all or part of the sequence of SEQ ID NO:9 and can include one or more of CDR1-light (SEQ ID NO:3), CDR2-light (SEQ ID NO:4) and CDR3-light (SEQ ID NO:5). Within the heavy chain, the variable domain includes all or part of the sequence of SEQ ID NO:10 and can include one or more of CDR1-heavy (SEQ ID NO:6), CDR2-heavy (SEQ ID NO:7) and CDR3-heavy (SEQ ID NO:8).

Described herein is an isolated antibody or an antigen-binding fragment thereof that specifically binds the antigen bound by an H1N1 antibody having a light chain consisting of the amino acid sequence of SEQ ID NO:1 and a heavy chain consisting of the amino acid sequence of SEQ ID NO:2. In various embodiments: the antibody or antigen-binding fragment thereof binds H1N1 (e.g., A/CA/04/2009 H1N1) with a Kd of equal to or less than $10^{-9}$, $10^{-10}$ or $6\times10^{-11}$); the antibody or antigen-binding fragment thereof binds recombinat HA from H1N1 (e.g., A/CA/04/2009 H1N1) with a Kd equal to or less than $10^{-9}$, $10^{-10}$ or $9\times10^{-11}$); the antibody comprises a light chain variable region comprising the amino acids sequences of SEQ ID NOs: 3, 4, and 5; the antibody comprises a heavy chain variable region comprising the amino acids sequences of SEQ ID NOs: 6, 7, and 8; the antibody is a human antibody; the antibody is an IgG antibody; the antibody is an IgG1 antibody; the antibody is an IgG1, kappa antibody; the antibody is an IgG1, lambda antibody; the antibody is selected from an IgM, IgA, IgD and IgE antibody; the antigen-binding fragment is selected from a Fab, a F(ab')2 fragment, a Fd fragment, an Fv fragment, and a dAb fragment; the antibody is a scFv.

Also described is an isolated antibody or antigen-binding fragment thereof wherein the antibody comprises: (a) polypeptide comprising the amino acid sequences of one or more of SEQ ID NOs: 3, 4, and 5; and (b) polypeptide comprising the amino acid sequences of one or more of SEQ ID NOs: 6, 7, and 8. In various embodiments: the isolated antibody or antigen-binding fragment thereof comprises: (a) polypeptide comprising the amino acid sequences of two or more of SEQ ID NOs: 3, 4, and 5; and (b) polypeptide comprising the amino acid sequences of two or more of SEQ ID NOs: 6, 7, and 8; the isolated antibody or antigen-binding fragment thereof comprises: (a) polypeptide comprising the amino acid sequences of SEQ ID NOs: 3, 4, and 5; and (b) polypeptide comprising the amino acid sequences of SEQ ID NOs: 6, 7, and 8; the isolated antibody or antigen-binding fragment thereof comprises a first polypeptide comprising, in the amino terminal to carboxy terminal direction amino acid sequences of two or more of SEQ ID NOs: 3, 4, and 5, wherein there are 10-20 amino acids between SEQ ID NOs: 3 and 4 and between SEQ ID NOs: 4 and 5; and a second polypeptide comprising, in the amino terminal to carboxy terminal direction amino acid sequences of two or more of SEQ ID NOs: 6, 7, and 8, wherein there are 10-20 amino acids between SEQ ID NOs: 6 and 7 and between SEQ ID NOs: 7 and 8: the antibody or antigen-binding fragment thereof binds H1N1 (e.g., A/CA/04/2009 H1N1) with a Kd of equal to or less than $10^{-9}$, $10^{-10}$ or $6\times10^{-11}$); the antibody or antigen-binding fragment thereof binds recombinat HA from H1N1 (e.g., A/CA/04/2009 H1N1) with a Kd equal to or less than $10^{-9}$, $10^{-10}$ or $9\times10^{-11}$); the antibody comprises a light chain variable region comprising the amino acids sequences of SEQ ID NOs: 3, 4, and 5; the antibody comprises a heavy chain variable region comprising the amino acids sequences of SEQ ID NOs: 6, 7, and 8; the antibody is a human antibody; the antibody is an IgG antibody; the antibody is an IgG1 antibody; the antibody is an IgG1, kappa antibody; the antibody is an IgG1, lambda antibody; the antibody is selected from an IgM, IgA, IgD and IgE antibody; the antigen-binding fragment is selected from a Fab, a F(ab')2 fragment, a Fd fragment, an Fv fragment, and a dAb fragment; the antibody is a scFv.

Also described is an isolated antibody or antigen-binding fragment thereof comprising a light chain variable region comprising SEQ ID NOs: 3, 4, and 5 and a heavy chain variable region comprising SEQ ID NOs: 6, 7, and 8. In various embodiments: In various embodiments: the antibody or antigen-binding fragment thereof binds H1N1 (e.g., A/CA/04/2009 H1N1) with a Kd of equal to or less than $10^{-9}$, $10^{-10}$ or $6\times10^{-11}$); the antibody or antigen-binding fragment thereof binds recombinat HA from H1N1 (e.g., A/CA/04/2009 H1N1) with a Kd equal to or less than $10^{-9}$, $10^{- encompassed by the general term antibody, including: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al, (1989) Nature 341:544 546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Single chain Fv and other forms of single chain antibodies, such as diabodies are also encompassed by the general term antibody. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444; Poljak et al. (1994) *Structure* 2:1121).

An antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) *Human Antibodies and Hybridomas* 6:93) and use of a cysteine residue, a marker peptide and a C-terminal polyhistidine tag to make bivalent and biotinylated scFv molecules (Kipriyanov et al. (1994) *Mol. Immunol.* 31:1047). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

Human antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs and in particular CDR3.

Recombinant antibodies are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (Taylor et al. (1992) Nucl. Acids Res. 20:6287) or antibodies prepared, expressed, created or isolated by any other means that involves splicing of human immunoglobulin gene sequences or variants thereof to other DNA sequences. Such recombinant human antibodies have variable and constant regions derived from human germline immunoglobulin sequences or variants thereof. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that may not naturally exist within the human antibody germline repertoire in vivo.

DESCRIPTION OF THE DRAWINGS

FIG. 3. The monoclonal antibody EM4C04 is highly specific for the swine H1N1 influenza hemagglutinin and displays HAI activity only to the swine H1N1 virus. (a) ELISA binding curves of the mAb EM4C04, comparing binding to whole virus with reactivity to viral mixtures or the annual vaccines as indicated, to purified virions or to recombinant hemagglutinin (rHA) from swine H1N1 versus other influenza strains. Calculated Kd values are shown in parenthesis above the graphs. Cocktail: A/Sal.Is./3/2006 (H1N1), A/WI/57/05 (H3N2), and B/Mal./2506/04, 2006/7 Vaccine: A/New Cal./20/90 (H1N1), A/WI/57/05 (H3N2), and B/Mal./2506/04, 2008/9 Vaccine: A/Brisb./59/2007 (H1N1), A/Brisb./10/2007 (H3N2), and B/FL/4/2006. (b) EM4C04 is able to immuno-precipitate recombinant from swine H1N1 HA protein. (c) EM4C04 displays HAI activity toward swine H1N1 but not to several other H1N1 strains tested as indicated.

SEQUENCE LISTING

The Sequence Listing is submitted as an ASCII text file [86975-88879-05_Sequence_Lisitng.txt, Mar. 30, 2012, 41.2 KB], which is incorporated by reference herein.

DETAILED DESCRIPTION

The studies described below analyzed the B cell responses in patients infected with swine H1N1 virus. As part of these studies we generated a panel of virus specific human monoclonal antibodies. These antibodies were isolated from plasmablasts that were activated by infection providing a means to directly evaluate the breadth and repertoire of the antibody response elicited by swine H1N1 virus. Interestingly, a majority of these antibodies also reacted with seasonal influenza viruses. In fact, several of the antibodies bound with higher affinity to past influenza strains than to the current swine H1N1 virus. These findings suggest that the swine H1N1 virus predominantly activated memory B cells previously generated against cross-reactive but non-protective epitopes present in annual influenza strains. Of the influenza specific antibodies generated five bound to recombinant hemagglutinin (HA) protein and of these only one antibody showed hemagglutination-inhibition (HAI) activity against the swine H1N1 influenza virus. In contrast to most of the other antibodies generated, this neutralizing antibody was highly specific for the swine H1N1 virus and did not cross-react with the other H1N1 influenza viruses, confirming that the critical HA active-site epitopes in this new virus are quite unique. In vivo experiments showed that this antibody was able to protect mice challenged with a lethal dose of mouse-adapted swine H1N1 influenza virus. Moreover, it was effective therapeutically even when administered 60 hours after infection and could thus potentially be developed as a therapeutic agent against the swine H1N1 influenza virus pandemic.

The novel 2009 pandemic swine H1N1 influenza virus is characterized by a unique genetic make-up[1,2,8] that results in little or no pre-existing serum antibody mediated protection against infection[7,9]. It is currently unclear what effect this has on the repertoire of responding B cells in infected patients and whether infection with this novel virus leads to activation of cross-reactive memory B cells or if the response is dominated by newly induced naive B cells. To analyze the repertoire of the responding B cells after infection and to generate monoclonal antibodies (mAbs) against the swine H1N1 influenza strain, we examined the B cell responses in five patients infected with swine H1N1 virus. The clinical details about these patients are given in the supplemental methods section. Blood samples were taken 1-2 weeks after onset of clinical symptoms and were used to isolate infection-induced plasmablasts ($CD19^+$, $CD20^-$, $CD3^-$, $CD38^{high}$ and $CD27^{high}$ cells) by flow cytometry based cell sorting (FIG. 1*a* shows a representative donor). Using an adapted single cell multiplex RT-PCR approach[10,11,12], we then identified the heavy and light chain immunoglobulin genes from each individual plasmablast from two of the five patients. These heavy and light chain fragment pairs were then used to express fully human monoclonal antibodies. In total, 25 out of the 53 (47%) antibodies generated in this fashion bound to purified whole swine H1N1 influenza (A/CA/04/2009) virus by ELISA (FIG. 1*b*). It is notable that the majority of antibodies induced by infection were low affinity; only five of the 53 isolated antibodies, had affinities $>^{10-9}$ by non-linear regression analysis of ELISA data. Further, as indicated in FIG. 1*c*, five of the 53 antibodies bound to recombinant hemagglutinin (rHA) from swine H1N1 influenza by ELISA, but only one of these mAbs (EM4C04) displayed HAI activity (FIG. 1*d*). We conclude from this analysis that a large proportion of virus specific plasmablasts in these patients were not producing neutralizing antibodies, and that the majority of the B cell response was in fact directed at non-HA proteins.

In order to determine how specific the antibody response was to the swine H1N1 virus strain, the 53 monoclonal antibodies were screened by ELISA for reactivity to various influenza antigens (FIG. 2). The bars in FIG. 2 indicate the area under the curve of ELISA binding data (FIG. 1*a*), thus providing an overview of both the maximal binding ($B_{max}$) and the persistence of binding with decreasing dilutions (affinity or $K_d$), allowing a relative comparison of each antibody to all antigens by column. It is notable that most of the antibodies were indeed cross-reactive with past strains of influenza virus, suggesting that they arose through the activation of cross-reactive memory B cells. In total, 47% ($^{25}/_{52}$) of the antibodies bound to swine H1N1 and 58% ($^{30}/_{52}$) bound to antigens from any of the influenza strains tested. In fact, 23% of the antibodies bound to past annual influenza strains with higher affinity than to the swine H1N1 strain (FIG. 2, asterisks). The plasmablasts expressing antibodies that were cross-reactive to past annual influenza strains had also accumulated significantly more mutations in the variable genes on average than the swine H1N1-specific B cells (FIG. 5). These findings suggest that the swine H1N1 strain predominantly activated memory B cells previously generated against cross-reactive but non-protective epitopes present in annual influenza virus strains.

Figure 1:
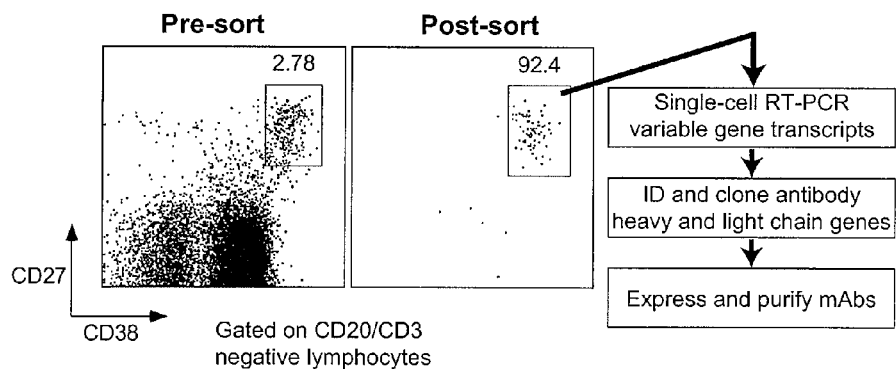
FIG. 1. Generation of human monoclonal antibodies against swine H1N1 influenza virus from plasmablasts of infected patients. (a) Antibody-secreting B cells in the PBMC of swine influenza virus infected patients were isolated by flow cytometry sorting based on their cell surface phenotype ($CD19^+$, $CD20^-$, $CD3^-$, $CD38^{high}$ and $CD27^{high}$). RT-PCR was used to isolate the variable genes from sorted single plasmablasts, which were then cloned into expression vectors and expressed in 293 cells as we have previously described[11, 12]. (b) Forty-seven percent (25/53) of the monoclonal antibodies generated bound to purified swine H1N1 (A/CA/04/2009) virus as determined by ELISA. (c) Five of 53 antibodies bound to recombinant swine H1N1 hemagglutinin (rHA), but only one of these mAbs (EM4C04) could inhibit hemagglutination (HAI+) of erythrocytes by the swine H1N1 influenza strain (d).
Figure 1:
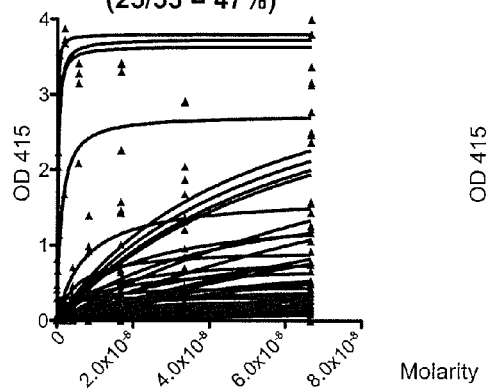
Figure 1:
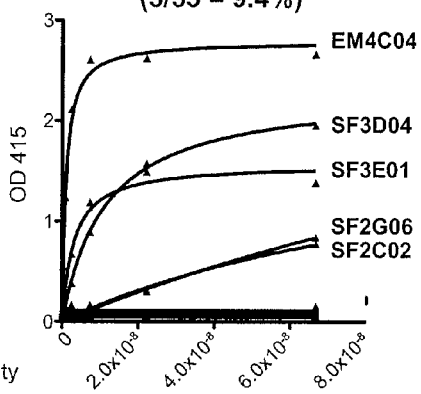
Figure 1:
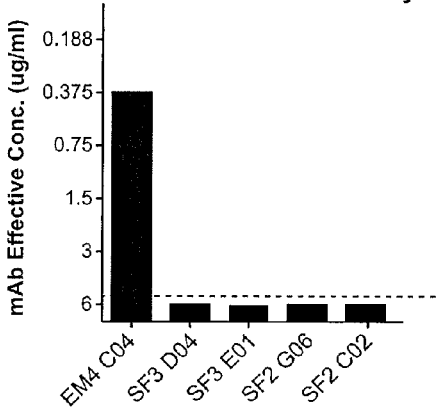
Figure 2:
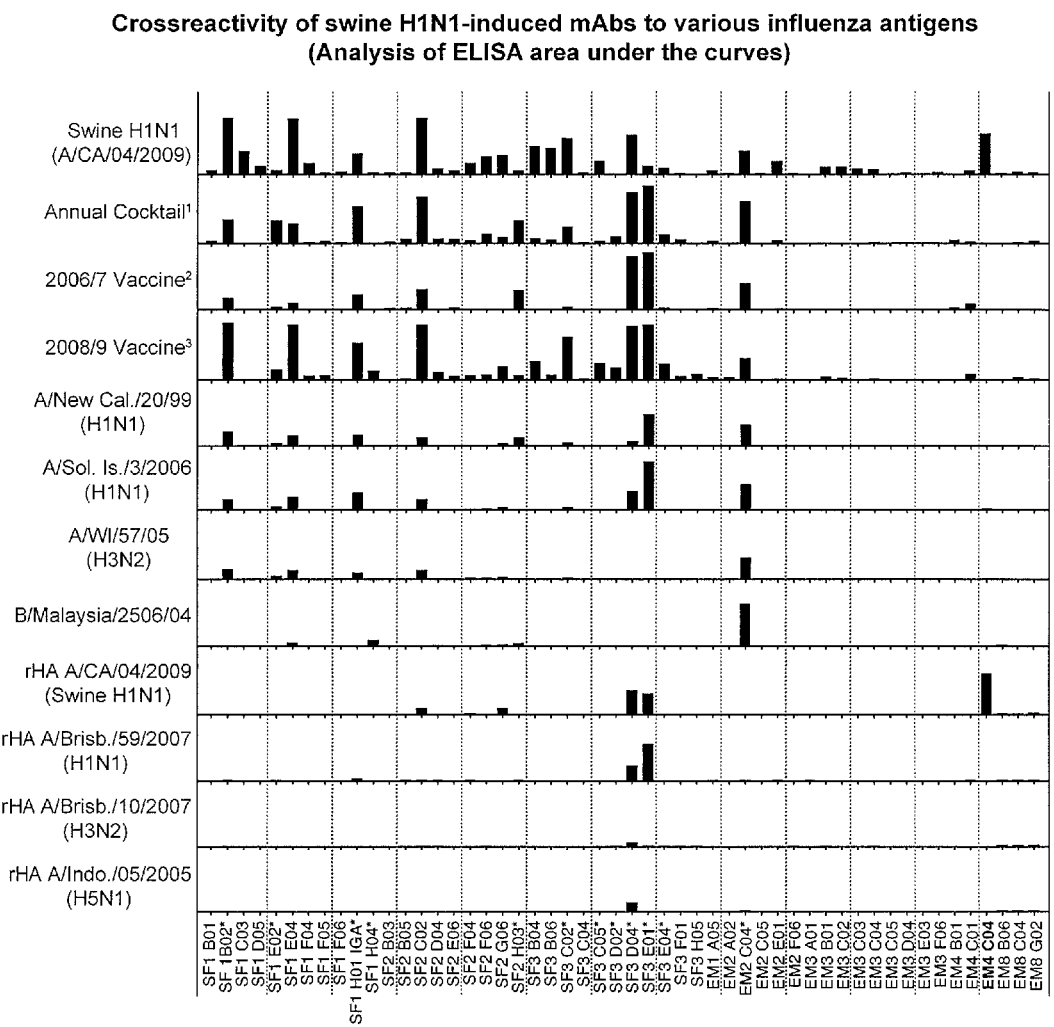
FIG. 2. A majority of the antibodies induced by swine H1N1 infection are crossreactive to seasonal influenza strains. Antibodies generated during active infection with the swine H1N1 strain (top line) were screened by ELISA for reactivity to various influenza antigens (indicated within the figure). Bars indicate the area under the curve, thus providing insight into both the maximal binding (Bmax) and persistence of binding with decreasing dilutions (affinity or Kd). Note that only a few antibodies were specific just to the swine H1N1 strain alone and that a number of antibodies bound to annual influenza vaccine strains either solely or with higher affinity (indicated with asterisks). In total 47% (25/52) bound swine H1N1 and 58% (30/52) bound influenza antigens at levels detectable by ELISA assay[12]. The mAb EM4C04 (bold) had the highest and most specific affinity against swine H1N1. Cocktail: A/Sal. Is./3/2006 (H1N1), A/WI/57/05 (H3N2), and B/Mal./2506/04, 2006/7 Vaccine: A/New Cal./20/90 (H1N1), A/WI/57/05 (H3N2), and B/Mal./2506/04, 2008/9 Vaccine: A/Brisb./59/2007 (H1N1), A/Brisb./10/2007 (H3N2), and B/FL/4/2006.
Figure 4:
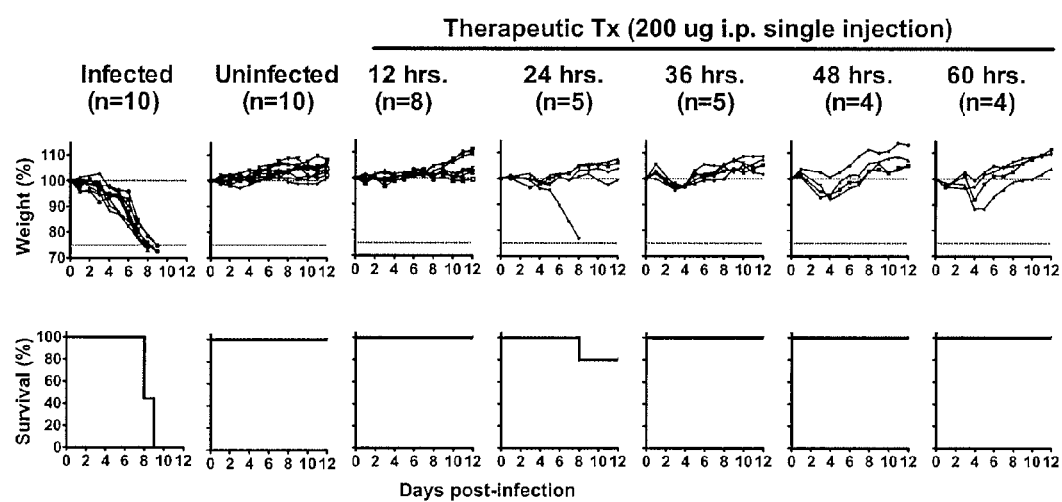
FIG. 4. EM4C04 has therapeutic efficacy in mice challenged with a lethal dose of mouse-adapted 2009 swine H1N1 influenza. 6-8 week old Balb/c mice were infected with a 3×LD50 dose of highly pathogenic, mouse-adapted 2009 swine H1N1 influenza (A/California/04/09). Subsequently, they were treated with 200 mg (10 mg/kg of body weight) EM4C04 human monoclonal antibody intraperitoneally at various time points (12, 24, 36, 48 and 60 hours) after infection. All mice were monitored daily for body weight changes and any signs of morbidity and mortality. Infected, untreated mice showed clear signs of sickness around day 4-5 post infection and perished by day 8-9. Upper panels show body weight change and the lower panels show survival curves.
Figure 5:
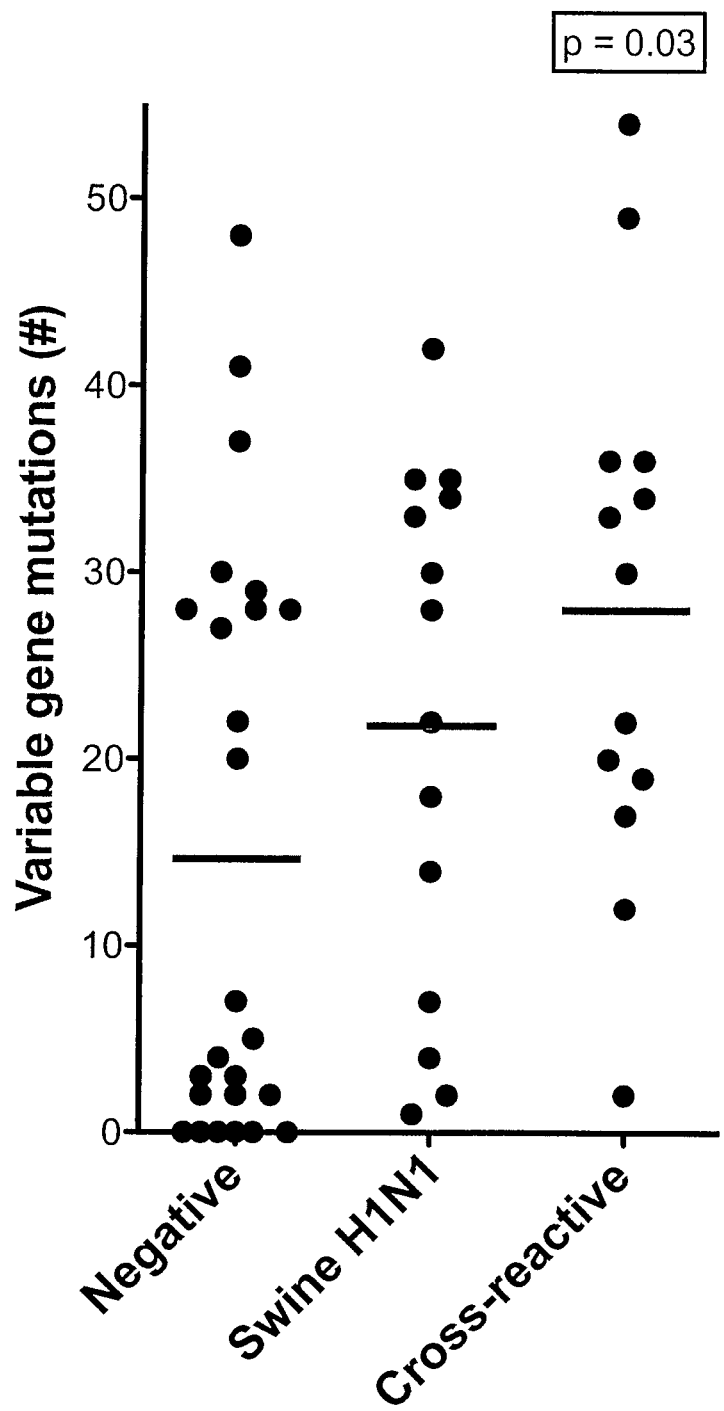
FIG. 5. Plasmablasts expressing antibodies that cross-react to annual influenza strains have accumulated more somatic hypermutations. The higher frequency of mutations in the more crossreactive antibodies indicate that they were derived from a recall response of memory B cells, originally induced by annual influenza viruses. It is also notable that a number of IgG+ plasmablasts that had no detectable binding to influenza by ELISA were from cells that had no mutations of the variable genes. The origin and specificity of these cells is unknown but they may be cells activated during a primary response against swine H1N1 epitopes that had affinities below the threshold of detection. The frequency of point mutations was determined from the variable gene sequences of the VH and Vκ sequences that were generated for the cloning and expression of the antibodies. Points represent the sum of heavy and light chain mutations. Statistical significance was determined by students t test.
Figure 6:
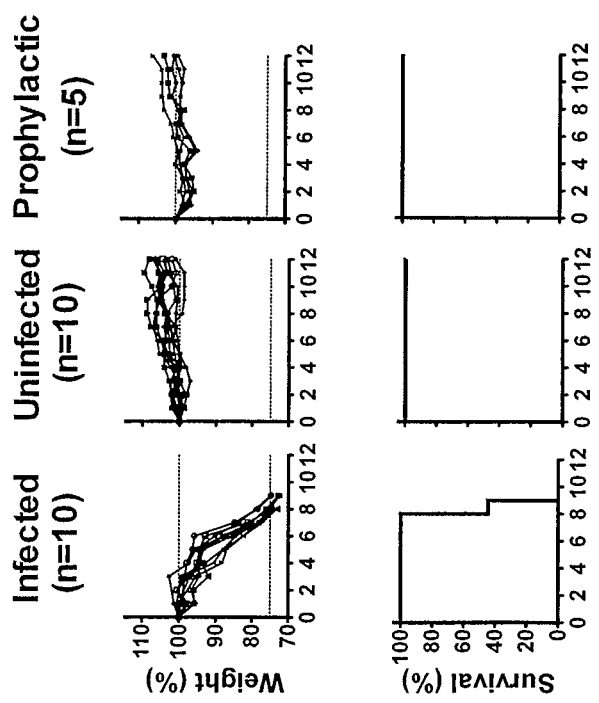
FIG. 6. Prophylactic treatment with EM4C04 can protect mice from a lethal challenge with mouse-adapted swine H1N1 influenza. 6-8 week old Balb/c mice were treated with 200 μg (10 mg/kg of body weight) EM4C04 human monoclonal antibody intraperitoneally 12 hours prior to infection with a 3×LD50 dose of highly pathogenic mouse adapted swine H1N1 influenza. All mice were monitored daily for body weight changes and any signs of morbidity and mortality. Upper panels show body weight change and the lower panels show survival curves.

It is worth noting that the sole HAI+mAb, EM4C04 (FIG. 2) was also the most specific against swine H1N1, demonstrating that the critical HA active-site epitopes are quite unique, as predicted by analyses of the HA amino acid sequences by several other groups[1,2,7,13]. The high specificity of EM4C04 demonstrates that this antibody could be valuable for diagnostic purposes for the pandemic swine H1N1 influenza virus (FIG. 3*a*). This antibody was also able to immuno-precipitate recombinant HA protein derived from swine H1N1 (FIG. 3*b*). In addition, while EM4C04 efficiently inhibited the agglutination of red blood cells by swine H1N1 virus, it had no HAI activity against several other influenza strains (FIG. 3*c*). The high affinity ($6.1x^{10-11}$ to purified virus and $9x^{10-11}$ to rHA) for the HA active site suggested that this antibody could be used for passive immunization to treat swine H1N1 influenza infection. We therefore tested the prophylactic and therapeutic potential of EM4C04 in mice infected with a lethal dosage of highly pathogenic, mouse-adapted swine H1N1 strain.

As indicated in FIG. 4 (and FIG. 6), the EM4C04 antibody is highly effective at either providing prophylactic protection against infection or to treat and facilitate clearance of a lethal dose of mouse-adapted swine H1N1 from 6-8 week old Balb/c mice. For the prophylactic experiments mice were pretreated with 200 μg EM4C04 human monoclonal antibody intraperitoneally and then challenged 12 hours later with a 3×LD50 dose of mouse-adapted novel H1N1 influenza (FIG. 6). To determine the therapeutic potential of EM4C04, mice were first challenged and then treated with antibody at various times after infection (FIG. 4). While untreated mice died 8-9 days after the infection, mice treated even as late as 60 hours after challenge survived. Infected mice treated at later time points were already showing measurable weight loss that was reversed by administration of the antibody, demonstrating therapeutic potential even after the onset of symptoms. Overall, 30 of 31 infected mice that were treated with EM4C04, irrespective of when they were treated, made a complete recovery from infection. It is likely that the therapeutic effects of EM4C04 treatment involve both direct viral neutralization as well as facilitation of endogenous cell-mediated immunity[14]. It is possible that the antibody treatment may reduce viral titers and thus allow the endogenous immune responses to catch up and subsequently clear the infection.

The studies show that the antibody responses induced in patients infected with the novel swine H1N1 influenza appear to be dominated by a recall response of non-protective memory B cells that are cross-reactive to annual influenza strains. Of the 25 virus-specific monoclonal antibodies generated herein only one displayed HAI activity against the swine H1N1 virus. This low frequency of cells producing protective antibodies after infection differs significantly as compared to previous work on seasonal influenza vaccines[12], where 40% of the virus specific antibodies bound with high affinity to HA and half of those antibodies had HAI activity against the influenza vaccine viral strains. As the novel swine H1N1 vaccine is now becoming widely available[15-18], it will be of interest to compare the vaccine induced antibody responses to the responses induced by infection as described herein. Finally, the in vivo protection experiments presented here demonstrate that the human monoclonal antibody EM4C04 has impressive prophylactic and therapeutic activity in mice and shows potential for development as a therapeutic agent against the pandemic swine H1N1 influenza virus in humans.

Methods

Patients were recruited with IRB approval and had ongoing or recent verified swine H1N1 infections. HAI titers, inhibiting antibody concentrations, and viral neutralization were determined by standard procedures as previously described[12,19]. The ASCs were identified herein as $CD3^-/CD20^{-/low}/CD19^+/CD27^{hi}/CD38^{hi}$ cells as previously described[11,12]. The single cell RT-PCR methods and the procedures for production of recombinant mAbs were as previously describee[10-12]. Monoclonal antibodies were screened against fresh influenza virions grown in chicken eggs. ELISA was performed on starting concentrations of 10 ug/ml of virus or rHA and on 1:20 dilution of the vaccines and antibody affinities (Kd) were calculated by nonlinear regression analysis as previously described[12]. For immunoprecipitation, 1 μg each of recombinant HA protein and antibody were incubated at 4° C. overnight in 100 μl NP40 Buffer prior to precipitation with Protein G-Sepharose. The samples were denatured for 5 min at 95° C. in Laemmli gel sample buffer followed by centrifugation to remove the Protein GSepharose and analysis on 12% Tris-Glycine polyacrylamide gels. Precipitated protein bands were identified by staining with Sypro-orange and Fluorescence imaging. For the challenge experiments, female Balb/c mice (8 weeks old) were challenged intra-nasally with $3{\times}xLD_{50}$ of a highly pathogenic, mouse-adapted swine H1N1 influenza virus (A/California/04/09) that was passaged in mice for five generations. Mice were treated intraperitoneally with 200 ug (10 mg/kg of body weight) of the specific mAb EM4C04 at all time points. All mice were monitored daily for morbidity and body weight changes.

Patients

All studies were approved by the Emory University, University of Chicago and Columbia University institutional review boards (Emory IRB#22371 and 555-2000, U of C IRB#16851E, CU IRB#AAAE1819). Patient 1 (EM) is a 30-year old healthy woman who developed fever, cough and progressive dyspnea over 8 days prior to hospital admission. She was diagnosed with acute respiratory syndrome (ARDS), which required mechanical ventilation. Her nasopharyngeal swab on admission was positive for influenza by RTPCR. She continued shedding virus (hospital day 13) despite treatment with oseltamivir, but had cleared the virus by day 15 with continued treatment. Her course was further complicated by bacterial pneumonia, pulmonary embolism, and a requirement for prolonged oscillatory ventilator support and tracheostomy. She gradually recovered and was discharged to home two months after becoming ill. Blood samples for PBMC preparation were collected 19 days and 29 days after the onset of symptoms. Patient 2 (SF) is a 37-year old man with a history of hypertension and interstitial lung disease of unknown etiology who was hospitalized with symptoms of fever, cough, shortness of breath, nausea and vomiting for 3 days. He was diagnosed with pneumonia, acute sinusitis and acute renal failure. His nasopharyngeal swab on admission was positive for influenza virus by culture and was confirmed as the swine H1N1 influenza virus by RTPCR. He was initially treated with oseltamivir for 5 days but was continuing to shed influenza virus and was discharged with a course of zanamivir. He was hospitalized for a total of 8 days and recovered. PBMCs were collected 18 days after the onset of symptoms. Patient 3 is a 25 year old male who developed cough and fever to 103° F. The diagnosis of 2009 H1N1 influenza was confirmed by RT-PCR. He was treated with oseltamivir and his symptoms lasted for 4 days. He recovered completely and blood samples were collected 9 days after the onset of symptoms. Patient 4 is a previously healthy, 40-year old man who developed symptoms consistent with mild upper respiratory tract illness, including cough, rhinorrhea, and fever. MassTag PCR analysis of a nasopharyngeal swab specimen obtained 6 days after symptom onset identified H1N1 influenza virus; the presence of swine H1N1 influenza virus was subsequently confirmed by RT-PCR. Blood samples for PBMC isolation were obtained 13 days after the onset of symptoms. Patient 5 is a 52 year old female whose diagnosis of 2009 H1N1 influenza A was confirmed by RT-PCR. Her symptoms included fever, cough, pharyngitis, myalgias, nausea, headache, and gastrointestinal symptoms. She was treated with oseltamivir and her symptoms resolved after 6 days and she recovered completely. Blood samples were collected 10 days after the onset of symptoms.

Cell and Serum Isolation

All work with samples from infected patients was performed in a designated BSL2+ facility at Emory University. Peripheral blood mononuclear cells (PBMC) were isolated using Vacutainer tubes (Becton Dickinson, BD), washed, and resuspended in PBS with 2% FCS for immediate use or frozen for subsequent analysis. Plasma samples were saved in −80C.

Viruses and Antigens

The Swine H1N1 influenza virus (A/California/04/2009) was kindly provided by Dr. Richard J Webby at St. Jude Childrens Hospital. Influenza virus stocks used for the assays were freshly grown in eggs, prepared and purified as described[19] and the hemagglutination activity (HA) was determined using turkey red blood cells (Lampire Biological Laboratories, Pipersville, Pa.) as previously described[12,19] or purchased as inactivated preparations (ProSpec-Tany TechnoGene Ltd., Rehovot, Israel) and included: A/California/04/2009 (H1N1), A/FM/1/47 (H1N1), A/PR8/34 (H1N1), A/New Jersey/76 (H1N1), A/New Caledonia/20/9 (H1N1), A/Solomon Island/3/2006, A/Wisconsin/67/2005 (H3N2), and B/Malaysia/2506/2004. Vaccines tested included the 2006/7 vaccine from Chiron Vaccines Limited (Liverpool, UK) and the 2008/9 formulation from Sanofi Pasteur Inc. (Swiftwater, Pa.). Recombinant HA proteins were provided by the influenza reagent resource (IRR; influenza reagent resource.org) of the CDC (rHA from A/California/04/2009 (H1N1) (#FR-180), A/Brisbane/10/2007 (H1N1) (#FR-61), A/Brisbane/59/2007 (H3N2) (#FR-65)) or by Biodefense & Emerging Infections research repository (BEI; www.beiresources.org) (rHA from A/Indonesia/05/2005).

Flow Cytometry Analysis and Cell Sorting

Analytical flow cytometry analysis was performed on whole blood following lysis of erythrocytes and fixing in 2% PFA. All live cell sorting was performed on purifiedPBMCs in the BSL-3 facility at the Emory Vaccine Center. All antibodies for bothanalytical and cell sorting cytometry were purchased from Pharmingen, except anti-CD27 that was purchased from ebiosciences. Anti-CD3-PECy7 or PerCP, anti-CD20-PECy7 or PerCP, anti-CD38-PE, anti-CD27-APC and anti-CD19-FITC. ASCs were gated and isolated as $CD19^+CD3^-CD20^{low}CD27^{high}CD38^{high}$ cells. Flow cytometry data was analyzed using FlowJo software.

Generation of Monoclonal Antibodies

Identification of antibody variable region genes were done essentially as previously described[10,11]. Briefly, single ASCs were sorted into 96-well PCR plates containing RNase inhibitor (Promega). VH and Vκ genes from each cell were amplified by RT-PCR and nested PCR reactions using cocktails of primers specific for both IgG and IgA as previously describee[10,11] and then sequenced. To generate recombinant antibodies, restriction sites were incorporated by PCR with primers to the particular variable and junctional genes. VH or Vκ genes amplified from each single cell were cloned into IgG1 or Igκ expression vectors as previously describee[10,11]. Heavy/light chain plasmids were co-transfected into the 293A cell line for expression and antibodies purified with protein A sepharose.

ELISA and HAI Assays

Whole virus, recombinant HA or vaccine-specific ELISA was performed on starting concentrations of 10 ug/ml of virus or rHA and on 1:20 dilution of the vaccine as previously described[12]. The hemagglutination inhibition (HAI) titers were determined as previously described[11,19]. Affinity estimates were calculated by nonlinear regression analysis of curves from 8 dilutions of antibody (10 to 0.125 µg/ml) using GraphPad Prism.

Immunoprecipitation

For immunoprecipitation, 100 µl NP40 Buffer (20 mM Tris-HCl PH8.0, 137 mM NaCl, 10% Glycerol, 1% NP-40, 2 mM EDTA) containing complete Protease Inhibitors (Roche) was mixed with 1 µg of recombinant HA protein and incubated on ice for 30 min. One microgram of monoclonal antibody was then added. The antibody and HA mixture was incubated at 4° C. overnight with constant agitation. On the next day, Protein G-Sepharose (GE Healthcare) was prepared in NP40 buffer at a volume of 10 µl/sample. Protein GSepharose was incubated with the antibody and HA mixture at 4C for 4 hrs with constant agitation. The protein G-Sepharose was centrifuged for 3 min at 3000 rpm and the pellet was washed with 400 µl of NP40 buffer for 3 times. Finally the pellet was resuspended into 25 µl of Laemmli gel sample buffer (Bio-Rad). The samples were then boiled for 5 min at 95 C. The protein G was pelleted and 15 µl of supernatant was loaded onto 12% Tris-Glycine polyacrylamide gels. The gels were run in 1×TGS at 70V for 30 min, followed by 120V till the frontline ran out of the gel. The gels were stained with 1× Sypro-orange (Invitrogen) in 7.5% acetic acid for 1 hr, and then gels were destained with 7.5% acetic acid for 3 min. Gels were finally scanned in a Typhoon 9410 Fluorescence imaging system (GE Healthcare).

In Vivo Protection Experiments

Female Balb/c mice 6-8 weeks old were used for the challenge studies. Mice were inoculated intra-nasally with $3xLD_{50}$ of a highly pathogenic, mouse-adapted swine H1N1 influenza virus (A/California/04/09) that was passaged in mice five generations. The $LD_{50}$ was determined by the method of Reed and Muench. The experiments were conducted in accordance with ethical procedures and policies approved by the Emory University's Institutional Animal Care and Use Committee. In order to determine the prophylactic efficacy of the mAb, mice were treated intraperitoneally with 200 μg (10 mg/kg of body weight) of the specific mAb EM4C04. Twelve hours later mice were challenged with 3xLD$_{50}$ of the mouse adapted H1N1 virus. All mice were monitored daily for any signs of morbidity and mortality. Body weight changes were registered daily for a period of 14 days. All mice that lost more that 25% of their initial body weight were sacrificed according to the IACUC guideless. In order to determine the therapeutic efficacy of the EM4C04 mAb, mice were challenged with 3xLD$_{50}$ of the mouse-adapted swine H1N1 virus. At various times post infection (12, 24, 36, 48, 60 hours) mice were treated intraperitoneally with 200 μg (10 mg/kg of body weight) of the specific mAb EM4C04. All mice were monitored daily and the body weight changes were registered daily as described above.

Statistical Analysis

Data was collected and graphed using MS Excel and Graphpad Prism software. Efficacy of the therapeutic and challenge experiments was evaluated by ANOVA using Graphpad Prism software.

Sequences of Antibodies

Described below are the sequences of the EM4C04 heavy chain and light chain

```
EM4C04 Heavy Chain Variable Region:
DNA
                                                            (SEQ ID NO: 11)
GAGGTGCAGCTGGTGGAGTCTGGGGGAGGCCTGGTCAAGCCTGGGGGGTCCCTGAGACTCTCCT

GTTCAGCCTCTGGATTCACCTTCAATATCTATGCCATGAACTGGGTCCGCCAGGTTCCAGGAAA

GGGGCTGGATTGGGTCTCATCCATTAGTAGTAGGGGTGATTACATATACTACGCAGAGTCAGTG

GAGGGCCGATTCACCATCTCCAGAGACAACGCCAAGAACTCACTGTATCTGGAAATGAACAGCC

TGAGAGCCGAGGACACGGCTGTGTATTACTGTGCGAGAGCTGGGCTGGGTACAGTGGATTTAAG

GTGGGGGGGGCCTTCGACCACTGGGGCAAGGGAATCCTGGTCACCGTCTCCTCA

Amino Acid:
                                                            (SEQ ID NO: 2)
EVQLVESGGGLVKPGGSLRLSCSASGFTFNIYAMNWVRQVPGKGLDWVSSISSRGDYIYYAESVE

GRFTISRDNAKNSLYLEMNSLRAEDTAVYYCARAGLGTVDLRWGGAFDHWGKGILVTVSS

Alignment:
Ig Sequence Name:EM-Swine1-4C04H-

V gene:         Z14073_IGHV3-21*01

D Gene:         None Found

D Gene 2:       None Found

J Gene:         X86355 IGHJ5*02

Clonal Pool:    0

CDR3 Length:    17

CDR3 AA:        RAGLGTVDLRWGGAFDH (SEQ ID NO: 12)

|> Z14073_1GHV3-21*01    20              30              40
                 E   V   Q   L   V   E   S   G   G   G   L   V   K   P   G
Germline        GAG GTG CAG CTG GTG GAG TCT GGG GGA GGC CTG GTC AAG CCT GGG
EM-Swine1-4C04H- --- --- --- --- --- --- --- --- --- --- --- --- --- --- ---

50              60              70              80              90
                 G   S   L   R   L   S   C   A   A   S   G   F   T   F   S
Germline        GGG TCC CTG AGA CTC TCC TGT GCA GCC TCT GGA TTC ACC TTC AGT
EM-Swine1-4C04H- --- --- --- --- --- --- --- T-- --- --- --- --- --- --- -A-
                                             S                               N 100             110             120             130
                 S   Y   S   M   N   W   V   R   Q   A   P   G   K   G   L
Germline        AGC TAT AGC ATG AAC TGG GTC CGC CAG GCT CCA GGG AAG GGG CTG
EM-Swine1-4C04H- -T- --- GC- --- --- --- --- --- --- -T- --- --A --- --- ---
                 I       A                                V 140             150             160             170             180
                 E   W   V   S   S   I   S   S   S   S   S   Y   I   Y   Y
Germline        GAG TGG GTC TCA TCC ATT AGT AGT AGT AGT AGT TAC ATA TAC TAC
EM-Swine1-4C04H- --T --- --- --- --- --- --- --- --G G-- GA- --- --- --- ---
                 D                                       R   G   D
```

```
                              -continued
                          190              200              210              220
                  A  D  S  V  K  G  R  F  T  I  S  R  D  N  A
Germline         GCA GAC TCA GTG AAG GGC CGA TTC ACC ATC TCC AGA GAC AAC GCC
EM-Swine1-4C04H- --- --G --- --- G-- --- --- --- --- --- --- --- --- --- ---
                      E             E 230              240              250              260              270
                  K  N  S  L  Y  L  Q  M  N  S  L  R  A  E  D
Germline         AAG AAC TCA CTG TAT CTG CAA ATG AAC AGC CTG AGA GCC GAG GAC
EM-Swine1-4C04H- --- --- --- --- --- --- G-- --- --- --- --- --- --- --- ---
                                          E 280              290              300              310
                  T  A  V  Y  Y  C  A  ?  ?  ?  ?  ?  ?  ?  ?
Germline         ACG GCT GTG TAT TAC TGT GCG AGN NNN NNN NNN NNN NNN NNN NNN
EM-Swine1-4C04H- --- --- --- --- --- --- --- --A GCT GGG CTG GGT ACA GTG GAT
                                                R   A   G   L   G   T   V   D 320              330    |> X86355 IGHJ5*02  350              360
                  ?  ?  ?  ?  ?  ?  F  D  P  W  G  Q  G  T  L
Germline         NNN NNN NNN NNN NNN NNN TTC GAC CCC TGG GGC CAG GGA ACC CTG
EM-Swine1-4C04H- TTA AGG TGG GGG GGG GCC --- --- -A- --- --- A-- --- -T- ---
                  L   R   W   G   G   A              H           K       I 370
                  V  T  V  S  S  ?  (SEQ ID NO: 14)
Germline         GTC ACC GTC TCC TCA G  (SEQ ID NO: 13)
EM-Swine1-4C04H- --- --- --- --- --- -  (SEQ ID NO: 15)
                                        (SEQ ID NO: 2)
```

EM4C04 kappa Variable Domain:
DNA
(SEQ ID NO: 16)

GACATCCAGATGACCCAGTCTCCATCCTCCCTGTCTGCATCTGTTGGAGACAGAGTCACCATCT

CTTGCCAGGCGAGTCAGGATATTACCAACTTTTTAAATTGGTACCAGCAGAAATCTGGGGAAGC

CCCTAAGCTCCTGATCTACGATGCATCCGATTTGGAAACAGGGGTCCCATCAAGGTTCAGTGGA

AGTGGATCTGGGACAGATTTTACTTTCACCATCAGCAGGCTGCAGCCTGAAGACACTGCAACAT

ATTACTGTCAACAGTATGACGATCTCCCGTATACTTTTGGCCAGGGGACCAAGGTGGAGATCAAA

Amino acid
(SEQ ID NO: 1)

DIQMTQSPSSLSASVGDRVTISCQASQDITNFLNWYQQKSGEAPKLLIYDASDLETGVPSRFSGS

GSGTDFTFTISRLQPEDTATYYCQQYDDLPYTFGQGTKVEIK

Alignment:
Ig Sequence Name:EM-Swine1-4C04K-

V gene:        M64855_IGKV1D-33*01

D Gene:        None Found

D Gene 2:      None Found

J Gene:        J00242 IGKJ2*01

Clonal Pool:   0

CDR3 Length:   8

CDR3 AA:       QYDDLPYT (SEQ ID NO: 17)

```
                 |> M64855_IGKV1D-33*01    20              30              40
                  D  I  Q  M  T  Q  S  P  S  S  L  S  A  S  V
Germline         GAC ATC CAG ATG ACC CAG TCT CCA TCC TCC CTG TCT GCA TCT GTA
EM-Swine1-4C04K- --- --- --- --- --- --- --- --- --- --- --- --- --- --- --T 50               60               70               80               90
                  G  D  R  V  T  I  T  C  Q  A  S  Q  D  I  S
Germline         GGA GAC AGA GTC ACC ATC ACT TGC CAG GCG AGT CAG GAC ATT AGC
EM-Swine1-4C04K- --- --- --- --- --- --- T-- --- --- --- --- --T --- -C- ---
                                          S                               T 100              110              120              130
                  N  Y  L  N  W  Y  Q  Q  K  P  G  K  A  P  K
Germline         AAC TAT TTA AAT TGG TAT CAG CAG AAA CCA GGG AAA GCC CCT AAG
EM-Swine1-4C04K- --- -T- --- --- --- --C --- --- T-T --- G-- --- --- --- ---
```

-continued

```
                                   F                     S      E
                  140            150          160          170          180
              L   L   I   Y   D   A   S   N   L   E   T   G   V   P   S
Germline      CTC CTG ATC TAC GAT GCA TCC AAT TTG GAA ACA GGG GTC CCA TCA
EM-Swine1-4C04K- --- --- --- --- --- --- --- G-- --- --- --- --- --- --- ---
                                              D 190          200          210          220
              R   F   S   G   S   G   S   G   T   D   F   T   F   T   I
Germline      AGG TTC AGT GGA AGT GGA TCT GGG ACA GAT TTT ACT TTC ACC ATC
EM-Swine1-4C04K- --- --- --- --- --- --- --- --- --- --- --- --- --- --- ---

230          240          250          260          270
              S   S   L   Q   P   E   D   I   A   T   Y   Y   C   Q   Q
Germline      AGC AGC CTG CAG CCT GAA GAT ATT GCA ACA TAT TAC TGT CAA CAG
EM-Swine1-4C04K- --- --G --- --- --- --- --C -C- --- --- --- --- --- --- ---
                      R                      T 280              |> J00242 IGKJ2*01      310
              Y   D   N   L   ?   ?   T   F   G   Q   G   T   K   L   E
Germline      TAT GAT AAT CTC CCN NNN ACT TTT GGC CAG GGG ACC AAG CTG GAG
EM-Swine1-4C04K- --- --C G-- --- --G TAT --- --- --- --- --- --- --- G-- ---
                      D       P   Y                                  V 320
              I   K   ?   (SEQ ID NO: 19)
Germline      ATC AAA C   (SEQ ID NO: 18)
EM-Swine1-4C04K- --- --- -   (SEQ ID NO: 20)
                          (SEQ ID NO: 1)
```

CDR and FR of EM4C04 Heavy Chain:
Nucleotide:
FW1:

(SEQ ID NO: 21)

GAGGTGCAGCTGGTGGAGTCTGGGGGAGGCCTGGTCAAGCCTGGGGGGTCCCTGAGACTCTCCT

GTTCAGCCTCTGGATTCACCTTCAAT

CDR1:

(SEQ ID NO: 22)

ATCTATGCCATGAAC

FW2:

(SEQ ID NO: 23)

TGGGTCCGCCAGGTTCCAGGAAAGGGGCTGGATTGGGTCTCA

CDR2:

(SEQ ID NO: 24)

TCCATTAGTAGTAGGGGTGATTACATATACTACGCAGAGTCAGTGGAGGGC

FW3:

(SEQ ID NO: 25)

CGATTCACCATCTCCAGAGACAACGCCAAGAACTCACTGTATCTGGAAATGAACAGCCTGAGAG

CCGAGGACACGGCTGTGTATTACTGTGCGAGA

CDR3:

(SEQ ID NO: 26)

GCTGGGCTGGGTACAGTGGATTTAAGGTGGGGGGGGGCCTTCGACCAC

FW4:

(SEQ ID NO: 27)

TGGGGCAAGGGAATCCTGGTCACCGTCTCCTCA

Amino Acids:
FW1:

(SEQ ID NO: 28)

EVQLVESGGGLVKPGGSLRLSCSASGFTFN

CDR1:

(SEQ ID NO: 6)

IYAMN

FW2:

(SEQ ID NO: 29)

WVRQVPGKGLDWVS

CDR2:

(SEQ ID NO: 7)

SISSRGDYIYYAESVEG

FW3:
(SEQ ID NO: 30)
RFTISRDNAKNSLYLEMNSLRAEDTAVYYCAR

CDR3:
(SEQ ID NO: 8)
AGLGTVDLRWGGAFDH

FW4:
(SEQ ID NO: 31)
WGKGILVTVSS

CDR and FR of EM4C04 Light Chain:
Nucleotide:
FW1:
(SEQ ID NO: 32)
GACATCCAGATGACCCAGTCTCCATCCTCCCTGTCTGCATCTGTTGGAGACAGAGTCACCATCT

CTTGCCAGGCGAGT

CDR1:
(SEQ ID NO: 33)
CAGGATATTACCAACTTTTTAAAT

FW2:
(SEQ ID NO: 34)
TGGTACCAGCAGAAATCTGGGGAAGCCCCTAAGCTCCTGATCTAC

CDR2:
(SEQ ID NO: 35)
GATGCATCCGATTTGGAAACA

FW3:
(SEQ ID NO: 36)
GGGGTCCCATCAAGGTTCAGTGGAAGTGGATCTGGGACAGATTTTACTTTCACCATCAGCAGGC

TGCAGCCTGAAGACACTGCAACATATTACTGT

CDR3:
(SEQ ID NO: 37)
CAACAGTATGACGATCTCCCGTATACT

FW4:
(SEQ ID NO: 38)
TTTGGCCAGGGGACCAAGGTGGAGATCAAA

Amino acids:
FW1:
(SEQ ID NO: 39)
DIQMTQSPSSLSASVGDRVTISC

CDR1:
(SEQ ID NO: 3)
QASQDITNFLN

FW2:
(SEQ ID NO: 40)
WYQQKSGEAPKLLIY

CDR2:
(SEQ ID NO: 4)
DASDLET

FW3:
(SEQ ID NO: 41)
GVPSRFSGSGSGTDFTFTISRLQPEDTATYYC

CDR3:
(SEQ ID NO: 5)
QQYDDLPYT

FW4:
(SEQ ID NO: 42)
FGQGTKVEIK

The CDR described herein can be grafted into the following vectors encoding human IgG and kappa chains, as well as others: Fully human IgG (GenBank® Accession No: FJ475055) and Fully human kappa (GenBank® Accession No: FJ475056).

GenBank ® FJ475055

(SEQ ID NO: 43)

RSTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK (SEQ ID NO: 44)

```
   1 ttcgagctcg cccgacattg attattgact agttattaat agtaatcaat tacggggtca
  61 ttagttcata gcccatatat ggagttccgc gttacataac ttacggtaaa tggcccgcct
 121 ggctgaccgc ccaacgaccc ccgcccattg acgtcaataa tgacgtatgt tcccatagta
 181 acgccaatag ggactttcca ttgacgtcaa tgggtggagt atttacggta aactgcccac
 241 ttggcagtac atcaagtgta tcatatgcca agtacgcccc ctattgacgt caatgacggt
 301 aaatggcccg cctggcatta tgcccagtac atgaccttat gggactttcc tacttggcag
 361 tacatctacg tattagtcat cgctattacc atggtgatgc ggttttggca gtacatcaat
 421 gggcgtggat agcggtttga ctcacgggga tttccaagtc tccaccccat tgacgtcaat
 481 gggagtttgt tttggcacca aaatcaacgg gactttccaa aatgtcgtaa caactccgcc
 541 ccattgacgc aaatgggcgg taggcgtgta cggtgggagg tctatataag cagagctcgt
 601 ttagtgaacc gtcagatcgc ctggagacgc catccacgct gttttgacct ccatagaaga
 661 caccgggacc gatccagcct ccgcggccgg aacggtgca ttggaacgcg gattccccgt
 721 gccaagagtg acgtaagtac cgcctataga gtctataggc ccacccccctt ggcttcgtta
 781 gaacgcggct acaattaata cataacctta tgtatcatac acatacgatt taggtgacac
 841 tatagaataa catccacttt gcctttctct ccacaggtgt ccactcccag gtccaactgc
 901 acctcggttc tatcgattga attccaccat gggatggtca tgtatcatcc ttttctagt
 961 agcaactgca accggtgtac actcgagcgt acggtcgacc aagggcccat cggtcttccc
1021 cctggcaccc tcctccaaga gcacctctgg gggcacagcg gccctgggct gcctggtcaa
1081 ggactacttc cccgaacctg tgacggtctc gtggaactca ggcgccctga ccagcggcgt
1141 gcacaccttc ccggctgtcc tacagtcctc aggactctac tccctcagca gcgtggtgac
1201 cgtgccctcc agcagcttgg gcacccagac ctacatctgc aacgtgaatc acaagcccag
1261 caacaccaag gtggacaaga agttgagcc caaatcttgt gacaaaactc acacatgccc
1321 accgtgccca gcacctgaac tcctgggggg accgtcagtc ttcctcttcc ccccaaaacc
1381 caaggacacc ctcatgatct cccggacccc tgaggtcaca tgcgtggtgg tggacgtgag
1441 ccacgaagac cctgaggtca agttcaactg gtacgtggac ggcgtggagg tgcataatgc
1501 caagacaaag ccgcgggagg agcagtacaa cagcacgtac cgtgtggtca gcgtcctcac
1561 cgtcctgcac caggactggc tgaatggcaa ggagtacaag tgcaaggtct ccaacaaagc
1621 cctcccagcc cccatcgaga aaaccatctc caaagccaaa gggcagcccc gagaaccaca
1681 ggtgtacacc ctgcccccat cccgggatga gctgaccaag aaccaggtca gcctgacctg
1741 cctggtcaaa ggcttctatc ccagcgacat cgccgtggag tgggagagca atgggcagcc
```

-continued

```
1801 ggagaacaac tacaagacca cgcctcccgt gctggactcc gacggctcct tcttcctcta
1861 cagcaagctc accgtggaca agagcaggtg cagcagggg aacgtcttct catgctccgt
1921 gatgcatgag gctctgcaca accactacac gcagaagagc ctctccctgt ctccgggtaa
1981 atgaagcttg gccgccatgg cccaacttgt ttattgcagc ttataatggt tacaaataaa
2041 gcaatagcat cacaaatttc acaaataaag cattttttc actgcattct agttgtggtt
2101 tgtccaaact catcaatgta tcttatcatg tctggatcga tcgggaatta attcggcgca
2161 gcaccatggc ctgaaataac ctctgaaaga ggaacttggt taggtacctt ctgaggcgga
2221 aagaaccagc tgtggaatgt gtgtcagtta gggtgtggaa agtccccagg ctccccagca
2281 ggcagaagta tgcaaagcat gcatctcaat tagtcagcaa ccaggtgtgg aaagtcccca
2341 ggctccccag caggcagaag tatgcaaagc atgcatctca attagtcagc aaccatagtc
2401 ccgcccctaa ctccgcccat cccgcccta actccgccca gttccgccca ttctccgccc
2461 catggctgac taatttttt tatttatgca gaggccgagg ccgcctcggc ctctgagcta
2521 ttccagaagt agtgaggagg cttttttgga ggcctaggct tttgcaaaaa gctgttaaca
2581 gcttggcact ggccgtcgtt ttacaacgtc gtgactggga aaaccctggc gttacccaac
2641 ttaatcgcct tgcagcacat ccccccttcg ccagctggcg taatagcgaa gaggcccgca
2701 ccgatcgccc ttcccaacag ttgcgtagcc tgaatggcga atggcgcctg atgcggtatt
2761 ttctccttac gcatctgtgc ggtatttcac accgcatacg tcaaagcaac catagtacgc
2821 gccctgtagc ggcgcattaa gcgcggcggg tgtggtggtt acgcgcagcg tgaccgctac
2881 acttgccagc gccctagcgc ccgctccttt cgctttcttc ccttcctttc tcgccacgtt
2941 cgccggcttt cccgtcaag ctctaaatcg gggctccct ttaggttcc gatttagtgc
3001 tttacggcac ctcgacccca aaaaacttga tttgggtgat ggttcacgta gtgggccatc
3061 gccctgatag acggttttc gccctttgac gttggagtcc acgttcttta atagtggact
3121 cttgttccaa actggaacaa cactcaaccc tatctcgggc tattcttttg atttataagg
3181 gattttgccg atttcggcct attggttaaa aaatgagctg atttaacaaa aatttaacgc
3241 gaattttaac aaaatattaa cgtttacaat tttatggtgc actctcagta caatctgctc
3301 tgatgccgca tagttaagcc aactccgcta tcgctacgtg actgggtcat ggctgcgccc
3361 cgacacccgc caacacccgc tgacgcgccc tgacgggctt gtctgctccc ggcatccgct
3421 tacagacaag ctgtgaccgt ctccgggagc tgcatgtgtc agaggttttc accgtcatca
3481 ccgaaacgcg cgaggcagta ttcttgaaga cgaaagggcc tcgtgatacg cctatttta
3541 taggttaatg tcatgataat aatggtttct tagacgtcag gtggcacttt tcggggaaat
3601 gtgcgcggaa cccctatttg tttatttttc taaatacatt caaatatgta tccgctcatg
3661 agacaataac cctgataaat gcttcaataa tattgaaaaa ggaagagtat gagtattcaa
3721 catttccgtg tcgcccttat tcccttttt gcggcatttt gccttcctgt ttttgctcac
3781 ccagaaacgc tggtgaaagt aaaagatgct gaagatcagt tgggtgcacg agtgggttac
3841 atcgaactgg atctcaacag cggtaagatc cttgagagtt ttcgccccga gaacgttt
3901 ccaatgatga gcacttttaa agttctgcta tgtggcgcgg tattatcccg tgatgacgcc
3961 gggcaagagc aactcggtcg ccgcatacac tattctcaga atgacttggt tgagtactca
4021 ccagtcacag aaaagcatct tacggatggc atgacagtaa gagaattatg cagtgctgcc
4081 ataaccatga gtgataacac tgcggccaac ttacttctga caacgatcgg aggaccgaag
4141 gagctaaccg cttttttgca caacatgggg gatcatgtaa ctcgccttga tcgttgggaa
```

-continued

```
4201 ccggagctga atgaagccat accaaacgac gagcgtgaca ccacgatgcc agcagcaatg
4261 gcaacaacgt tgcgcaaact attaactggc gaactactta ctctagcttc ccggcaacaa
4321 ttaatagact ggatggaggc ggataaagtt gcaggaccac ttctgcgctc ggcccttccg
4381 gctggctggt ttattgctga taaatctgga gccggtgagc gtgggtctcg cggtatcatt
4441 gcagcactgg ggccagatgg taagccctcc cgtatcgtag ttatctacac gacggggagt
4501 caggcaacta tggatgaacg aaatagacag atcgctgaga taggtgcctc actgattaag
4561 cattggtaac tgtcagacca agtttactca tatatacttt agattgattt aaaacttcat
4621 ttttaattta aaaggatcta ggtgaagatc ctttttgata atctcatgac caaaatccct
4681 taacgtgagt tttcgttcca ctgagcgtca gaccccgtag aaaagatcaa aggatcttct
4741 tgagatcctt ttttttctgcg cgtaatctgc tgcttgcaaa caaaaaaacc accgctacca
4801 gcggtggttt gtttgccgga tcaagagcta ccaactcttt ttccgaaggt aactggcttc
4861 agcagagcgc agataccaaa tactgtcctt ctagtgtagc cgtagttagg ccaccacttc
4921 aagaactctg tagcaccgcc tacatacctc gctctgctaa tcctgttacc agtggctgct
4981 gccagtggcg ataagtcgtg tcttaccggg ttggactcaa gacgatagtt accggataag
5041 gcgcagcggt cgggctgaac ggggggttcg tgcacacagc ccagcttgga gcgaacgacc
5101 tacaccgaac tgagatacct acagcgtgag cattgagaaa gcgccacgct tcccgaaggg
5161 agaaaggcgg acaggtatcc ggtaagcggc agggtcggaa caggagagcg cacgagggag
5221 cttccagggg gaaacgcctg gtatctttat agtcctgtcg ggtttcgcca cctctgactt
5281 gagcgtcgat ttttgtgatg ctcgtcaggg gggcggagcc tatggaaaaa cgccagcaac
5341 gcggcctttt tacggttcct ggccttttgc tggccttttg ctcacatgtt ctttcctgcg
5401 ttatcccctg attctgtgga taaccgtatt accgcctttg agtgagctga taccgctcgc
5461 cgcagccgaa cgaccgagcg cagcgagtca gtgagcgagg aagcggaaga gcgcccaata
5521 cgcaaaccgc ctctccccgc gcgttggccg attcattaat ccagctggca cgacaggttt
5581 cccgactgga aagcgggcag tgagcgcaac gcaattaatg tgagttacct cactcattag
5641 gcacccagg ctttacactt tatgcttccg gctcgtatgt tgtgtggaat tgtgagcgga
5701 taacaatttc acacaggaaa cagctatgac catgattacg aattaa
```

GenBank® FJ475056

(SEQ ID NO: 45)
MSIQHFRVALIPFFAAFCLPVFAHPETLVKVKDAEDQLGARVGYIELDLNSGKILE
SFRPEERFPMMSTFKVLLCGAVLSRDDAGQEQLGRRIHYSQNDLVEYSPVTEKHLT
DGMTVRELCSAAITMSDNTAANLLLTTIGGPKELTAFLHNMGDHVTRLDRWEPELN
EAIPNDERDTTMPAAMATTLRKLLTGELLTLASRQQLIDWMEADKVAGPLLRSALP
AGWFIADKSGAGERGSRGIIAALGPDGKPSRIVVIYTTGSQATMDERNRQIAEIGA
SLIKHW (SEQ ID NO: 46)
```
  1 ttcgagctcg cccgacattg attattgact agttattaat agtaatcaat tacgggtca
 61 ttagttcata gcccatatat ggagttccgc gttacataac ttacggtaaa tggcccgcct
121 ggctgaccgc ccaacgaccc ccgcccattg acgtcaataa tgacgtatgt tcccatagta
181 acgccaatag ggactttcca ttgacgtcaa tgggtggagt atttacggta aactgcccac
241 ttggcagtac atcaagtgta tcatatgcca agtacgcccc ctattgacgt caatgacggt
301 aaatggcccg cctggcatta tgcccagtac atgaccttat gggactttcc tacttggcag
361 tacatctacg tattagtcat cgctattacc atggtgatgc ggttttggca gtacatcaat
```

-continued

```
 421 gggcgtggat agcggtttga ctcacgggga tttccaagtc tccaccccat tgacgtcaat
 481 gggagtttgt tttggcacca aaatcaacgg gactttccaa aatgtcgtaa caactccgcc
 541 ccattgacgc aaatgggcgg taggcgtgta cggtgggagg tctatataag cagagctcgt
 601 ttagtgaacc gtcagatcgc ctggagacgc catccacgct gttttgacct ccatagaaga
 661 caccgggacc gatccagcct ccgcggccgg gaacggtgca ttggaacgcg gattccccgt
 721 gccaagagtg acgtaagtac cgcctataga gtctataggc ccaccccctt ggcttcgtta
 781 gaacgcggct acaattaata cataaccctta tgtatcatac acatacgatt taggtgacac
 841 tatagaataa catccacttt gcctttctct ccacaggtgt ccactcccag gtccaactgc
 901 acctcggttc tatcgattga attccaccat gggatggtca tgtatcatcc ttttctagt
 961 agcaactgca accggtgtac actcgagcgt acggtggctg caccatctgt cttcatcttc
1021 ccgccatctg atgagcagtt gaaatctgga actgcctctg ttgtgtgcct gctgaataac
1081 ttctatccca gagaggccaa agtacagtgg aaggtggata acgccctcca atcgggtaac
1141 tcccaggaga gtgtcacaga gcaggacagc aaggacagca cctacagcct cagcagcacc
1201 ctgacgctga gcaaagcaga ctacgagaaa cacaaagtct acgcctgcga agtcacccat
1261 cagggcctga gctcgcccgt cacaaagagc ttcaacaggg gagagtgtta aagcttggc
1321 cgccatggcc caacttgttt attgcagctt ataatggtta caaataaagc aatagcatca
1381 caaatttcac aaataaagca ttttttttcac tgcattctag ttgtggtttg tccaaactca
1441 tcaatgtatc ttatcatgtc tggatcgatc gggaattaat tcggcgcagc accatggcct
1501 gaaataacct ctgaaagagg aacttggtta ggtaccttct gaggcggaaa gaaccagctg
1561 tggaatgtgt gtcagttagg gtgtggaaag tccccaggct ccccagcagg cagaagtatg
1621 caaagcatgc atctcaatta gtcagcaacc aggtgtggaa agtccccagg ctccccagca
1681 ggcagaagta tgcaaagcat gcatctcaat tagtcagcaa ccatagtccc gcccctaact
1741 ccgcccatcc cgcccctaac tccgcccagt tccgcccatt ctccgcccca tggctgacta
1801 attttttta tttatgcaga ggccgaggcc gcctcggcct ctgagctatt ccagaagtag
1861 tgaggaggct ttttggagg cctaggcttt tgcaaaaagc tgttaacagc ttggcactgg
1921 ccgtcgtttt acaacgtcgt gactgggaaa accctggcgt tacccaactt aatcgccttg
1981 cagcacatcc cccttcgcc agctggcgta atagcgaaga ggcccgcacc gatcgccctt
2041 cccaacagtt gcgtagcctg aatggcgaat ggcgcctgat gcggtatttt ctccttacgc
2101 atctgtgcgg tatttcacac cgcatacgtc aaagcaacca tagtacgcgc cctgtagcgg
2161 cgcattaagc gcggcgggtg tggtggttac gcgcagcgtg accgctacac ttgccagcgc
2221 cctagcgccc gctcctttcg ctttcttccc ttcctttctc gccacgttcg ccggctttcc
2281 ccgtcaagct ctaaatcggg gctccctttt agggttccga tttagtgctt tacggcacct
2341 cgaccccaaa aaacttgatt tgggtgatgg ttcacgtagt gggccatcgc cctgatagac
2401 ggttttcgc cctttgacgt tggagtccac gttctttaat agtggactct tgttccaaac
2461 tggaacaaca ctcaacccta tctcgggcta ttcttttgat ttataaggga ttttgccgat
2521 ttcggcctat tggttaaaaa atgagctgat ttaacaaaaa tttaacgcga atttaacaa
2581 aatattaacg tttacaattt tatggtgcac tctcagtaca atctgctctg atgccgcata
2641 gttaagccaa ctccgctatc gctacgtgac tgggtcatgg ctgcgcccg acacccgcca
2701 acacccgctg acgcgccctg acgggcttgt ctgctcccgg catccgctta cagacaagct
2761 gtgaccgtct ccgggagctg catgtgtcag aggttttcac cgtcatcacc gaaacgcgcg
2821 aggcagtatt cttgaagacg aaagggcctc gtgatacgcc tatttttata ggttaatgtc
```

-continued

```
2881 atgataataa tggtttctta gacgtcaggt ggcacttttc ggggaaatgt gcgcggaacc
2941 cctatttgtt tattttttcta aatacattca aatatgtatc cgctcatgag acaataaccc
3001 tgataaatgc ttcaataata ttgaaaaagg aagagtatga gtattcaaca tttccgtgtc
3061 gcccttattc ccttttttgc ggcattttgc cttcctgttt ttgctcaccc agaaacgctg
3121 gtgaaagtaa aagatgctga agatcagttg ggtgcacgag tgggttacat cgaactggat
3181 ctcaacagcg gtaagatcct tgagagtttt cgccccgaag aacgttttcc aatgatgagc
3241 acttttaaag ttctgctatg tggcgcggta ttatcccgtg atgacgccgg gcaagagcaa
3301 ctcggtcgcc gcatacacta ttctcagaat gacttggttg agtactcacc agtcacagaa
3361 aagcatctta cggatggcat gacagtaaga gaattatgca gtgctgccat aaccatgagt
3421 gataacactg cggccaactt acttctgaca acgatcggag gaccgaagga gctaaccgct
3481 tttttgcaca acatggggga tcatgtaact cgccttgatc gttgggaacc ggagctgaat
3541 gaagccatac caaacgacga gcgtgacacc acgatgccag cagcaatggc aacaacgttg
3601 cgcaaactat taactggcga actacttact ctagcttccc ggcaacaatt aatagactgg
3661 atggaggcgg ataaagttgc aggaccactt ctgcgctcgg cccttccggc tggctggttt
3721 attgctgata aatctggagc cggtgagcgt gggtctcgcg gtatcattgc agcactgggg
3781 ccagatggta agccctcccg tatcgtagtt atctacacga cggggagtca ggcaactatg
3841 gatgaacgaa atagacagat cgctgagata ggtgcctcac tgattaagca ttggtaactg
3901 tcagaccaag tttactcata tatactttag attgatttaa aacttcattt ttaatttaaa
3961 aggatctagg tgaagatcct ttttgataat ctcatgacca aaatccctta acgtgagttt
4021 tcgttccact gagcgtcaga ccccgtagaa aagatcaaag gatcttcttg agatcctttt
4081 tttctgcgcg taatctgctg cttgcaaaca aaaaaaccac cgctaccagc ggtggttttgt
4141 ttgccggatc aagagctacc aactcttttt ccgaaggtaa ctggcttcag cagagcgcag
4201 ataccaaata ctgtccttct agtgtagccg tagttaggcc accacttcaa gaactctgta
4261 gcaccgccta catacctcgc tctgctaatc ctgttaccag tggctgctgc cagtggcgat
4321 aagtcgtgtc ttaccgggtt ggactcaaga cgatagttac cggataaggc gcagcggtcg
4381 ggctgaacgg ggggttcgtg cacacagccc agcttggagc gaacgaccta caccgaactg
4441 agatacctac agcgtgagca ttgagaaagc gccacgcttc ccgaagggag aaaggcggac
4501 aggtatccgg taagcggcag ggtcggaaca ggagagcgca cgagggagct tccagggga
4561 aacgcctggt atctttatag tcctgtcggg tttcgccacc tctgacttga gcgtcgattt
4621 ttgtgatgct cgtcaggggg gcggagccta tggaaaaacg ccagcaacgc ggccttttta
4681 cggttcctgg ccttttgctg gccttttgct cacatgttct ttcctgcgtt atcccctgat
4741 tctgtggata accgtattac cgcctttgag tgagctgata ccgctcgccg cagccgaacg
4801 accgagcgca gcgagtcagt gagcgaggaa gcggaagagc gcccaatacg caaaccgcct
4861 ctccccgcgc gttggccgat tcattaatcc agctggcacg acaggtttcc cgactggaaa
4921 gcgggcagtg agcgcaacgc aattaatgtg agttacctca ctcattaggc acccaggct
4981 ttacacttta tgcttccggc tcgtatgttg tgtggaattg tgagcggata acaatttcac
5041 acaggaaaca gctatgacca tgattacgaa ttaa
```

Use of Antibodies

Antibodies described herein can be used in any method that antibodies produced by other means cane be used. Thus, they can be used in passive therapy and diagnosis. Passive antibody immunization can provide a state of immediate immunity that can last for weeks and possibly months. Some human IgG isotypes have serum half-lives in excess of 30 days, which would confer long-lived protection to passively immunized persons. Where active vaccines are available, they may be administered together with antibodies to both immediate and long-lasting protection. In addition, the antibodies can be administered in conjunction with one or more therapeutic drugs for treatment or prevention of infection or for treatment of infection. Administration of antibodies produced as described herein will follow the general protocols for passive immunization. Antibodies for administration be prepare in a formulation suitable for administration to a host. Aqueous compositions comprise an effective amount of an antibody dispersed in a pharmaceutically acceptable carrier and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutical active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

Antibodies will generally be formulated for parenteral administration, e.g., formulated for injection via the intravenous, intramuscular, sub-cutaneous, intralesional, or even intraperitoneal routes. Upon formulation, solutions will be administered in a manner compatible with the dosage formulation or in such amount as is therapeutically effective. Some variation in dosage will necessarily occur depending on the condition of the subject being treated. The person responsible for administration will, in any event, determine the appropriate dose for the individual subject.

REFERENCES

1. Dawood, F. S., et al. Emergence of a novel swine-origin influenza A (H1N1) virus in humans. *N Engl J Med* 360, 2605-2615 (2009).
2. Garten, R. J., et al. Antigenic and genetic characteristics of swine-origin 2009 A(H1N1) influenza viruses circulating in humans. *Science* 325, 197-201 (2009).
3. Webby, R. J. & Webster, R. G. Are we ready for pandemic influenza? *Science* 302, 1519-1522 (2003).
4. Yen, H. L. & Webster, R. G. Pandemic influenza as a current threat. *Curr Top Microbiol Immunol* 333, 3-24 (2009).
5. Palese, P. Influenza: old and new threats. *Nat Med* 10, S82-87 (2004).
6. Steel, J., et al. Transmission of pandemic H1N1 influenza virus and impact of prior exposure to seasonal strains or interferon treatment. *J Virol* (2009).
7. Hancock, K., et al. Cross-Reactive Antibody Responses to the 2009 Pandemic H1N1 Influenza Virus. *N Engl J Med* (2009).
8. Brockwell-Staats, C., Webster, R. G. & Webby, R. J. Diversity of Influenza Viruses in Swine and the Emergence of a Novel Human Pandemic Influenza A (H1N1). *Influenza Other Respi Viruses* 3, 207-213 (2009).
9. Ahmed, R., Oldstone, M. B. & Palese, P. Protective immunity and susceptibility to infectious diseases: lessons from the 1918 influenza pandemic. *Nat Immunol* 8, 1188-1193 (2007).
10. Wardemann, H. et al. Predominant autoantibody production by early human B cell precursors. *Science* 301, 1374-1377 (2003).
11. Smith, K., et al. Rapid generation of fully human monoclonal antibodies specific to a vaccinating antigen. *Nat Protoc* 4, 372-384 (2009).
12. Wrammert, J., et al. Rapid cloning of high-affinity human monoclonal antibodies against influenza virus. *Nature* 453, 667-671 (2008).
13. Itoh Y., et al., In vitro and in vivo characterization of new swine-origin H1N1 influenza viruses. *Nature* 460, 1021-1025 (2009).
14. Doherty, P. C., Turner, S. J., Webby, R. G. & Thomas, P. G. Influenza and the challenge for immunology. *Nat Immunol* 7, 449-455 (2006).
15. Clark, T. W., et al. Trial of Influenza A (H1N1) 2009 Monovalent MF59-Adjuvanted Vaccine—Preliminary Report. *N Engl J Med* (2009).
16. Greenberg, M. E., et al. Response after One Dose of a Monovalent Influenza A (H1N1) 2009 Vaccine—Preliminary Report. *N Engl J Med* (2009).
17 Rappuoli, R., et al. Public health. Rethinking influenza. *Science* 326, 50 (2009).
18. Horimoto, T. & Kawaoka, Y. Designing vaccines for pandemic influenza. *Curr Top Microbiol Immunol* 333, 165-176 (2009).
19. Compans, R. W. Hemagglutination-inhibition: rapid assay for neuraminic acid-containing viruses. *J. Virol* 14, 1307-1309 (1974).

What is claimed is:

1. A non-naturally occurring chimeric monoclonal antibody, wherein the antibody comprises a heavy chain having a variable and constant region and a light chain having a variable and constant region, wherein the light chain variable region comprises CDR1 of SEQ ID NO: 3, CDR2 of SEQ ID NO: 4 and CDR3 of SEQ ID NO: 5 and wherein the heavy chain variable region comprises CDR1 of SEQ ID NO: 6, CDR2 of SEQ ID NO: 7 and CDR3 of SEQ ID NO: 8, and wherein the antibody specifically binds H1N1.

2. The non-naturally occurring chimeric monoclonal antibody of claim 1 wherein the antibody has Kd for purified H1N1 that is less than $1 \times 10^{-9}$.

3. A composition comprising a non-naturally occurring chimeric monoclonal antibody wherein the antibody comprises a heavy chain having a variable and constant region and a light chain having a variable and constant region, wherein the light chain variable region comprises CDR1 of SEQ ID NO: 3, CDR2 of SEQ ID NO: 4 and CDR3 of SEQ ID NO: 5 and wherein the heavy chain variable region comprises CDR1 of SEQ ID NO: 6, CDR2 of SEQ ID NO: 7 and CDR3 of SEQ ID NO: 8, and wherein the antibody specifically binds H1N1, and a pharmaceutically acceptable carrier.

4. A method for reducing the risk of infection with H1N1 in a human subject, the method comprising administering a non-naturally occurring chimeric monoclonal antibody comprising a heavy chain having a variable and constant region and a light chain having a variable and constant region, wherein the light chain variable region comprises CDR1 of SEQ ID NO: 3, CDR2 of SEQ ID NO: 4 and CDR3 of SEQ ID NO: 5 and wherein the heavy chain variable region comprises CDR1 of SEQ ID NO: 6, CDR2 of SEQ ID NO: 7 and CDR3 of SEQ ID NO: 8, specifically binds H1N1, to the human subject thereby reducing the risk of infection of H1N1 in the human subject.

5. A method for treating a patient infected with H1N1 virus, the method comprising administering a non-naturally occurring chimeric monoclonal antibody comprising a heavy chain having a variable and constant region and a light chain having a variable and constant region, wherein the light chain variable region comprises CDR1 of SEQ ID NO: 3, CDR2 of SEQ ID NO: 4 and CDR3 of SEQ ID NO: 5 and wherein the heavy chain variable region comprises CDR1 of SEQ ID NO: 6, CDR2 of SEQ ID NO: 7 and CDR3 of SEQ ID NO: 8, and wherein the antibody specifically binds H1N1, to the patient infected with the H1N1 virus, thereby treating the patient.

6. The non-naturally occurring chimeric monoclonal antibody of claim 1, or the antigen binding fragment thereof, wherein the heavy chain variable region consists of the amino acid sequence of SEQ ID NO: 2.

7. The non-naturally occurring chimeric monoclonal antibody of claim 1, or antigen binding fragment thereof, wherein the light chain variable region consists of the amino acid sequence of SEQ ID NO: 1.

8. The non-naturally occurring chimeric monoclonal antibody of claim 1, or the antigen binding fragment thereof, wherein the heavy chain variable region comprises the amino acid sequence of SEQ ID NO: 2 and the light chain variable region comprises the amino acid sequence of SEQ ID NO: 1.

9. A non-naturally occurring chimeric monoclonal antibody, wherein the antibody comprises a heavy chain having a variable and constant region and a light chain having a variable and constant region, wherein the light chain variable region comprises CDR1 of SEQ ID NO: 3, CDR2 of SEQ ID NO: 4 and CDR3 of SEQ ID NO: 5 and wherein the heavy chain variable region comprises CDR1 of SEQ ID NO: 6, CDR2 of SEQ ID NO: 7 and CDR3 of SEQ ID NO: 8, wherein the heavy chain constant region comprises SEQ ID NO: 43, and wherein the antibody specifically binds H1N1.

10. A non-naturally occurring monoclonal antibody specifically binding influenza virus H1N1, having a heavy chain with a constant domain and variable domain, and light chain with a variable domain and constant domain wherein the light chain variable region comprises CDR1 of SEQ ID NO: 3, CDR2 of SEQ ID NO: 4 and CDR3 of SEQ ID NO: 5 and the heavy chain variable region comprises CDR1 of SEQ ID NO: 6, CDR2 of SEQ ID NO: 7 and CDR3 of SEQ ID NO: 8, and wherein the heavy chain comprises a sequence that is different from any sequences present in naturally derived antibodies for which the light chain variable region comprises CDR1 of SEQ ID NO: 3, CDR2 of SEQ ID NO: 4 and CDR3 of SEQ ID NO: 5 and the heavy chain variable region comprises CDR1 of SEQ ID NO: 6, CDR2 of SEQ ID NO: 7 and CDR3 of SEQ ID NO: 8.

* * * * *

SEQUENCE LISTING

```
<160> NUMBER OF SEQ ID NOS: 46

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Ser Cys Gln Ala Ser Gln Asp Ile Thr Asn Phe
            20                  25                  30
```

```
Leu Asn Trp Tyr Gln Gln Lys Ser Gly Glu Ala Pro Lys Leu Leu Ile
            35                  40                  45

Tyr Asp Ala Ser Asp Leu Glu Thr Gly Val Pro Ser Arg Phe Ser Gly
        50                  55                  60

Ser Gly Ser Gly Thr Asp Phe Thr Phe Thr Ile Ser Arg Leu Gln Pro
65                  70                  75                  80

Glu Asp Thr Ala Thr Tyr Tyr Cys Gln Gln Tyr Asp Asp Leu Pro Tyr
                85                  90                  95

Thr Phe Gly Gln Gly Thr Lys Val Glu Ile Lys
            100                 105

<210> SEQ ID NO 2
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Thr Phe Asn Ile Tyr
            20                  25                  30

Ala Met Asn Trp Val Arg Gln Val Pro Gly Lys Gly Leu Asp Trp Val
            35                  40                  45

Ser Ser Ile Ser Ser Arg Gly Asp Tyr Ile Tyr Tyr Ala Glu Ser Val
        50                  55                  60

Glu Gly Arg Phe Thr Ile Ser Arg Asp Asn Ala Lys Asn Ser Leu Tyr
65                  70                  75                  80

Leu Glu Met Asn Ser Leu Arg Ala Glu Asp Thr Ala Val Tyr Tyr Cys
                85                  90                  95

Ala Arg Ala Gly Leu Gly Thr Val Asp Leu Arg Trp Gly Gly Ala Phe
            100                 105                 110

Asp His Trp Gly Lys Gly Ile Leu Val Thr Val Ser Ser
        115                 120                 125

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ala Ser Gln Asp Ile Thr Asn Phe Leu Asn
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ala Ser Asp Leu Glu Thr
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Gln Tyr Asp Asp Leu Pro Tyr Thr
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Tyr Ala Met Asn
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ile Ser Ser Arg Gly Asp Tyr Ile Tyr Tyr Ala Glu Ser Val Glu
1               5                   10                  15

Gly

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Gly Leu Gly Thr Val Asp Leu Arg Trp Gly Gly Ala Phe Asp His
1               5                   10                  15

<210> SEQ ID NO 9

<400> SEQUENCE: 9

000

<210> SEQ ID NO 10

<400> SEQUENCE: 10

000

<210> SEQ ID NO 11
<211> LENGTH: 375
<212> TYPE: DNA
<213> ORGANISM: Artificial Sequence
<220> FEATURE:
<223> OTHER INFORMATION: Description of Artificial Sequence: Synthetic
```

-continued

```
            polynucleotide

<400> SEQUENCE: 11
gaggtgcagc tggtggagtc tgggggaggc ctggtcaagc ctggggggtc cctgagactc      60
tcctgttcag cctctggatt caccttcaat atctatgcca tgaactgggt ccgccaggtt     120
ccaggaaagg ggctggattg ggtctcatcc attagtagta ggggtgatta catatactac     180
gcagagtcag tggagggccg attcaccatc tccagagaca acgccaagaa ctcactgtat     240
ctggaaatga acagcctgag agccgaggac acggctgtgt attactgtgc gagagctggg     300
ctgggtacag tggatttaag gtgggggggg gccttcgacc actggggcaa gggaatcctg     360
gtcaccgtct cctca                                                      375

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Gly Leu Gly Thr Val Asp Leu Arg Trp Gly Gly Ala Phe Asp
1               5                   10                  15

His

<210> SEQ ID NO 13
<211> LENGTH: 376
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(375)
<220> FEATURE:
<221> NAME/KEY: modified_base
<222> LOCATION: (294)..(333)
<223> OTHER INFORMATION: a, c, t, g, unknown or other

<400> SEQUENCE: 13 gag gtg cag ctg gtg gag tct ggg gga ggc ctg gtc aag cct ggg ggg       48
Glu Val Gln Leu Val Glu Ser Gly Gly Gly Leu Val Lys Pro Gly Gly
1               5                   10                  15 tcc ctg aga ctc tcc tgt gca gcc tct gga ttc acc ttc agt agc tat       96
Ser Leu Arg Leu Ser Cys Ala Ala Ser Gly Phe Thr Phe Ser Ser Tyr
            20                  25                  30 agc atg aac tgg gtc cgc cag gct cca ggg aag ggg ctg gag tgg gtc      144
Ser Met Asn Trp Val Arg Gln Ala Pro Gly Lys Gly Leu Glu Trp Val
        35                  40                  45 tca tcc att agt agt agt agt agt tac ata tac tac gca gac tca gtg      192
Ser Ser Ile Ser Ser Ser Ser Ser Tyr Ile Tyr Tyr Ala Asp Ser Val
    50                  55                  60 aag ggc cga ttc acc atc tcc aga gac aac gcc aag aac tca ctg tat      240
Lys Gly Arg Phe Thr Ile Ser Arg Asp Asn Ala Lys Asn Ser Leu Tyr
65                  70                  75                  80 ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                85                  90                  95 gcg agn nnn nnn nnn nnn nnn nnn nnn nnn nnn nnn nnn nnn ttc          336
Ala Xaa Xaa Xaa Xaa Xaa Xaa Xaa Xaa Xaa Xaa Xaa Xaa Xaa Phe
                100                 105                 110
```

```
gac ccc tgg ggc cag gga acc ctg gtc acc gtc tcc tca g            376
Asp Pro Trp Gly Gln Gly Thr Leu Val Thr Val Ser Ser
            115                 120                 125
```

<210> SEQ ID NO 14
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (98)..(98)
<223> OTHER INFORMATION: Arg or Ser
<220> FEATURE:
<221> NAME/KEY: MOD_RES
<222> LOCATION: (99)..(111)
<223> OTHER INFORMATION: Any amino acid

<400> SEQUENCE: 14

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Xaa Xaa Xaa Xaa Xaa Xaa Xaa Xaa Xaa Xaa Xaa Xaa Xaa Xaa Phe
            100                 105                 110

Asp Pro Trp Gly Gln Gly Thr Leu Val Thr Val Ser Ser
            115                 120                 125
```

<210> SEQ ID NO 15
<211> LENGTH: 376
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(375)

<400> SEQUENCE: 15

```
gag gtg cag ctg gtg gag tct ggg gga ggc ctg gtc aag cct ggg ggg    48
Glu Val Gln Leu Val Glu Ser Gly Gly Gly Leu Val Lys Pro Gly Gly
1               5                   10                  15 tcc ctg aga ctc tcc tgt tca gcc tct gga ttc acc ttc aat atc tat    96
Ser Leu Arg Leu Ser Cys Ser Ala Ser Gly Phe Thr Phe Asn Ile Tyr
            20                  25                  30 gcc atg aac tgg gtc cgc cag gtt cca gga aag ggg ctg gat tgg gtc   144
Ala Met Asn Trp Val Arg Gln Val Pro Gly Lys Gly Leu Asp Trp Val
        35                  40                  45 tca tcc att agt agt agg ggt gat tac ata tac tac gca gag tca gtg   192
Ser Ser Ile Ser Ser Arg Gly Asp Tyr Ile Tyr Tyr Ala Glu Ser Val
    50                  55                  60 gag ggc cga ttc acc atc tcc aga gac aac gcc aag aac tca ctg tat   240
```

```
                Glu Gly Arg Phe Thr Ile Ser Arg Asp Asn Ala Lys Asn Ser Leu Tyr
                 65                  70                  75                  80 ctg gaa atg aac agc ctg aga gcc gag gac acg gct gtg tat tac tgt      288
Leu Glu Met Asn Ser Leu Arg Ala Glu Asp Thr Ala Val Tyr Tyr Cys
                 85                  90                  95 gcg aga gct ggg ctg ggt aca gtg gat tta agg tgg ggg ggg gcc ttc      336
Ala Arg Ala Gly Leu Gly Thr Val Asp Leu Arg Trp Gly Gly Ala Phe
            100                 105                 110 gac cac tgg ggc aag gga atc ctg gtc acc gtc tcc tca g                376
Asp His Trp Gly Lys Gly Ile Leu Val Thr Val Ser Ser
        115                 120                 125

<210> SEQ ID NO 16
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gacatccaga tgacccagtc tccatcctcc ctgtctgcat ctgttggaga cagagtcacc       60
atctcttgcc aggcgagtca ggatattacc aactttttaa attggtacca gcagaaatct      120
ggggaagccc ctaagctcct gatctacgat gcatccgatt tggaaacagg ggtcccatca      180
aggttcagtg gaagtggatc tgggacagat tttactttca ccatcagcag gctgcagcct      240
gaagacactg caacatatta ctgtcaacag tatgacgatc tcccgtatac ttttggccag      300
gggaccaagg tggagatcaa a                                                321

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Tyr Asp Asp Leu Pro Tyr Thr
1               5

<210> SEQ ID NO 18
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(321)
<220> FEATURE:
<221> NAME/KEY: modified_base
<222> LOCATION: (285)..(288)
<223> OTHER INFORMATION: a, c, t, g, unknown or other

<400> SEQUENCE: 18 gac atc cag atg acc cag tct cca tcc tcc ctg tct gca tct gta gga        48
Asp Ile Gln Met Thr Gln Ser Pro Ser Ser Leu Ser Ala Ser Val Gly
1                5                  10                  15 gac aga gtc acc atc act tgc cag gcg agt cag gac att agc aac tat       96
Asp Arg Val Thr Ile Thr Cys Gln Ala Ser Gln Asp Ile Ser Asn Tyr
            20                  25                  30 tta aat tgg tat cag cag aaa cca ggg aaa gcc cct aag ctc ctg atc      144
```

-continued

```
Leu Asn Trp Tyr Gln Gln Lys Pro Gly Lys Ala Pro Lys Leu Leu Ile
         35                  40                  45 tac gat gca tcc aat ttg gaa aca ggg gtc cca tca agg ttc agt gga    192
Tyr Asp Ala Ser Asn Leu Glu Thr Gly Val Pro Ser Arg Phe Ser Gly
     50                  55                  60 agt gga tct ggg aca gat ttt act ttc acc atc agc agc ctg cag cct    240
Ser Gly Ser Gly Thr Asp Phe Thr Phe Thr Ile Ser Ser Leu Gln Pro
 65                  70                  75                  80 gaa gat att gca aca tat tac tgt caa cag tat gat aat ctc ccn nnn    288
Glu Asp Ile Ala Thr Tyr Tyr Cys Gln Gln Tyr Asp Asn Leu Pro Xaa
                 85                  90                  95 act ttt ggc cag ggg acc aag ctg gag atc aaa c                      322
Thr Phe Gly Gln Gly Thr Lys Leu Glu Ile Lys
            100                 105
```

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (96)..(96)
<223> OTHER INFORMATION: Any amino acid

<400> SEQUENCE: 19

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Xaa
                 85                  90                  95

Thr Phe Gly Gln Gly Thr Lys Leu Glu Ile Lys
            100                 105
```

<210> SEQ ID NO 20
<211> LENGTH: 322
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(321)

<400> SEQUENCE: 20

```
gac atc cag atg acc cag tct cca tcc tcc ctg tct gca tct gtt gga     48
Asp Ile Gln Met Thr Gln Ser Pro Ser Ser Leu Ser Ala Ser Val Gly
 1               5                  10                  15 gac aga gtc acc atc tct tgc cag gcg agt cag gat att acc aac ttt     96
Asp Arg Val Thr Ile Ser Cys Gln Ala Ser Gln Asp Ile Thr Asn Phe
             20                  25                  30 tta aat tgg tac cag cag aaa tct ggg gaa gcc cct aag ctc ctg atc    144
Leu Asn Trp Tyr Gln Gln Lys Ser Gly Glu Ala Pro Lys Leu Leu Ile
```

|  | | | | | | | | | | | | | | | | |
|---|---|---|---|---|---|---|---|---|---|---|---|---|---|---|---|---|
|  | | | 35 | | | | | 40 | | | | | 45 | | | |
| tac | gat | gca | tcc | gat | ttg | gaa | aca | ggg | gtc | cca | tca | agg | ttc | agt | gga | 192 |
| Tyr | Asp | Ala | Ser | Asp | Leu | Glu | Thr | Gly | Val | Pro | Ser | Arg | Phe | Ser | Gly |  |
|  | | 50 | | | | | 55 | | | | | 60 | | | | |
| agt | gga | tct | ggg | aca | gat | ttt | act | ttc | acc | atc | agc | agg | ctg | cag | cct | 240 |
| Ser | Gly | Ser | Gly | Thr | Asp | Phe | Thr | Phe | Thr | Ile | Ser | Arg | Leu | Gln | Pro |  |
| 65 | | | | | 70 | | | | | 75 | | | | | 80 | |
| gaa | gac | act | gca | aca | tat | tac | tgt | caa | cag | tat | gac | gat | ctc | ccg | tat | 288 |
| Glu | Asp | Thr | Ala | Thr | Tyr | Tyr | Cys | Gln | Gln | Tyr | Asp | Asp | Leu | Pro | Tyr |  |
|  | | | | 85 | | | | | 90 | | | | | 95 | | |
| act | ttt | ggc | cag | ggg | acc | aag | gtg | gag | atc | aaa | c | | | | | 322 |
| Thr | Phe | Gly | Gln | Gly | Thr | Lys | Val | Glu | Ile | Lys | | | | | | |
|  | | | | 100 | | | | 105 | | | | | | | | |

<210> SEQ ID NO 21
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaggtgcagc tggtggagtc tgggggaggc ctggtcaagc ctggggggtc cctgagactc    60
tcctgttcag cctctggatt caccttcaat                                     90

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
atctatgcca tgaac                                                     15

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgggtccgcc aggttccagg aaagggggctg gattgggtct ca                      42

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tccattagta gtagggggtga ttacatatac tacgcagagt cagtggaggg c             51

<210> SEQ ID NO 25
<211> LENGTH: 96
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 25
cgattcacca tctccagaga caacgccaag aactcactgt atctggaaat gaacagcctg     60
agagccgagg acacggctgt gtattactgt gcgaga                               96

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gctgggctgg gtacagtgga tttaaggtgg ggggggcct tcgaccac                   48

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tggggcaagg gaatcctggt caccgtctcc tca                                  33

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Thr Phe Asn
            20                  25                  30

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Val Arg Gln Val Pro Gly Lys Gly Leu Asp Trp Val Ser
1               5                   10

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Arg Phe Thr Ile Ser Arg Asp Asn Ala Lys Asn Ser Leu Tyr Leu Glu
1               5                   10                  15

Met Asn Ser Leu Arg Ala Glu Asp Thr Ala Val Tyr Tyr Cys Ala Arg
            20                  25                  30

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Trp Gly Lys Gly Ile Leu Val Thr Val Ser Ser
1               5                   10

<210> SEQ ID NO 32
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gacatccaga tgacccagtc tccatcctcc ctgtctgcat ctgttggaga cagagtcacc    60
atctcttgcc aggcgagt                                                 78

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
caggatatta ccaactttt aaat                                           24

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tggtaccagc agaaatctgg ggaagcccct aagctcctga tctac                   45

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gatgcatccg atttggaaac a                                             21

<210> SEQ ID NO 36
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 36 gggtcccat caaggttcag tggaagtgga tctgggacag attttacttt caccatcagc    60
aggctgcagc ctgaagacac tgcaacatat tactgt    96

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
caacagtatg acgatctccc gtatact    27

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tttggccagg ggaccaaggt ggagatcaaa    30

<210> SEQ ID NO 39
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Ile Gln Met Thr Gln Ser Pro Ser Ser Leu Ser Ala Ser Val Gly
1               5                   10                  15

Asp Arg Val Thr Ile Ser Cys
            20

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Tyr Gln Gln Lys Ser Gly Glu Ala Pro Lys Leu Leu Ile Tyr
1               5                   10                  15

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Val Pro Ser Arg Phe Ser Gly Ser Gly Ser Gly Thr Asp Phe Thr
1               5                   10                  15

Phe Thr Ile Ser Arg Leu Gln Pro Glu Asp Thr Ala Thr Tyr Tyr Cys

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Phe Gly Gln Gly Thr Lys Val Glu Ile Lys
1               5                   10

<210> SEQ ID NO 43
<211> LENGTH: 330
<212> TYPE: PRT
<213> ORGANISM: Homo sapiens

<400> SEQUENCE: 43

Arg Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn

|  |  | 290 |  |  | 295 |  |  | 300 |  |
| --- | --- | --- | --- | --- | --- | --- | --- | --- | --- |

Val Phe Ser Cys Ser Val Met His Glu Ala Leu His Asn His Tyr Thr
305             310             315             320

Gln Lys Ser Leu Ser Leu Ser Pro Gly Lys
                325             330

<210> SEQ ID NO 44
<211> LENGTH: 5746
<212> TYPE: DNA
<213> ORGANISM: Homo sapiens

<400> SEQUENCE: 44

```
ttcgagctcg cccgacattg attattgact agttattaat agtaatcaat tacggggtca      60
ttagttcata gcccatatat ggagttccgc gttacataac ttacggtaaa tggcccgcct     120
ggctgaccgc ccaacgaccc ccgcccattg acgtcaataa tgacgtatgt tcccatagta     180
acgccaatag ggactttcca ttgacgtcaa tgggtggagt atttacggta aactgcccac     240
ttggcagtac atcaagtgta tcatatgcca agtacgcccc ctattgacgt caatgacggt     300
aaatggcccg cctggcatta tgcccagtac atgaccttat gggactttcc tacttggcag     360
tacatctacg tattagtcat cgctattacc atggtgatgc ggttttggca gtacatcaat     420
gggcgtggat agcggtttga ctcacgggga tttccaagtc tccaccccat tgacgtcaat     480
gggagtttgt tttggcacca aaatcaacgg gactttccaa aatgtcgtaa caactccgcc     540
ccattgacgc aaatgggcgg taggcgtgta cggtgggagg tctatataag cagagctcgt     600
ttagtgaacc gtcagatcgc ctggagacgc catccacgct gttttgacct ccatagaaga     660
caccgggacc gatccagcct ccgcggccgg gaacggtgca ttggaacgcg gattccccgt     720
gccaagagtg acgtaagtac cgcctataga gtctataggc ccaccccctt ggcttcgtta     780
gaacgcggct acaattaata cataacctta tgtatcatac acatacgatt taggtgacac     840
tatagaataa catccacttt gcctttctct ccacaggtgt ccactcccag gtccaactgc     900
acctcggttc tatcgattga attccaccat gggatggtca tgtatcatcc tttttctagt     960
agcaactgca accggtgtac actcgagcgt acgtcgacc aagggcccat cggtcttccc    1020
cctggcaccc tcctccaaga gcacctctgg gggcacagcg ccctgggct gcctggtcaa    1080
ggactacttc cccgaacctg tgacggtctc gtggaactca ggcgccctga ccagcggcgt    1140
gcacaccttc ccggctgtcc tacagtcctc aggactctac tccctcagca gcgtggtgac    1200
cgtgccctcc agcagcttgg gcacccagac ctacatctgc aacgtgaatc acaagcccag    1260
caacaccaag gtggacaaga agttgagcc aaatcttgt gacaaaactc acacatgccc    1320
accgtgccca gcacctgaac tcctgggggg accgtcagtc ttcctcttcc cccaaaaacc    1380
caaggacacc ctcatgatct cccggacccc tgaggtcaca tgcgtggtgg tggacgtgag    1440
ccacgaagac cctgaggtca agttcaactg gtacgtggac ggcgtggagg tgcataatgc    1500
caagacaaag ccgcgggagg agcagtacaa cagcacgtac cgtgtggtca gcgtcctcac    1560
cgtcctgcac caggactggc tgaatggcaa ggagtacaag tgcaaggtct ccaacaaagc    1620
cctcccagcc cccatcgaga aaaccatctc caaagccaaa gggcagcccc gagaaccaca    1680
ggtgtacacc ctgcccccat cccgggatga gctgaccaag aaccaggtca gcctgacctg    1740
cctggtcaaa ggcttctatc ccagcgacat cgccgtggag tgggagagca atgggcagcc    1800
ggagaacaac tacaagacca cgcctcccgt gctggactcc gacggctcct tcttcctcta    1860
cagcaagctc accgtggaca agagcaggtg gcagcagggg aacgtcttct catgctccgt    1920
```

```
gatgcatgag gctctgcaca accactacac gcagaagagc ctctccctgt ctccgggtaa   1980
atgaagcttg gccgccatgg cccaacttgt ttattgcagc ttataatggt tacaaataaa   2040
gcaatagcat cacaaatttc acaaataaag catttttttc actgcattct agttgtggtt   2100
tgtccaaact catcaatgta tcttatcatg tctggatcga tcgggaatta attcggcgca   2160
gcaccatggc ctgaaataac ctctgaaaga ggaacttggt taggtacctt ctgaggcgga   2220
aagaaccagc tgtggaatgt gtgtcagtta gggtgtggaa agtccccagg ctccccagca   2280
ggcagaagta tgcaaagcat gcatctcaat tagtcagcaa ccaggtgtgg aaagtcccca   2340
ggctccccag caggcagaag tatgcaaagc atgcatctca attagtcagc aaccatagtc   2400
ccgcccctaa ctccgcccat cccgccccta actccgccca gttccgccca ttctccgccc   2460
catggctgac taattttttt tatttatgca gaggccgagg ccgcctcggc ctctgagcta   2520
ttccagaagt agtgaggagg cttttttgga ggcctaggct tttgcaaaaa gctgttaaca   2580
gcttggcact ggccgtcgtt ttacaacgtc gtgactggga aaaccctggc gttacccaac   2640
ttaatcgcct tgcagcacat ccccccttcg ccagctggcg taatagcgaa gaggcccgca   2700
ccgatcgccc ttcccaacag ttgcgtagcc tgaatggcga atggcgcctg atgcggtatt   2760
ttctccttac gcatctgtgc ggtatttcac accgcatacg tcaaagcaac catagtacgc   2820
gccctgtagc ggcgcattaa gcgcggcggg tgtggtggtt acgcgcagcg tgaccgctac   2880
acttgccagc gccctagcgc ccgctccttt cgctttcttc ccttcctttc tcgccacgtt   2940
cgccggcttt ccccgtcaag ctctaaatcg ggggctccct ttagggttcc gatttagtgc   3000
tttacggcac ctcgacccca aaaaacttga tttgggtgat ggttcacgta gtgggccatc   3060
gccctgatag acggtttttc gccctttgac gttggagtcc acgttcttta atagtggact   3120
cttgttccaa actggaacaa cactcaaccc tatctcgggc tattcttttg atttataagg   3180
gattttgccg atttcggcct attggttaaa aatgagctga tttaacaaa atttaacgc    3240 gaattttaac aaaatattaa cgtttacaat tttatggtgc actctcagta caatctgctc   3300
tgatgccgca tagttaagcc aactccgcta tcgctacgtg actgggtcat ggctgcgccc   3360
cgacacccgc caacacccgc tgacgcgccc tgacgggctt gtctgctccc ggcatccgct   3420
tacagacaag ctgtgaccgt ctccgggagc tgcatgtgtc agaggttttc accgtcatca   3480
ccgaaacgcg cgaggcagta ttcttgaaga cgaaagggcc tcgtgatacg cctattttta   3540
taggttaatg tcatgataat aatggtttct tagacgtcag gtggcacttt tcggggaaat   3600
gtgcgcggaa cccctatttg tttatttttc taaatacatt caaatatgta tccgctcatg   3660
agacaataac cctgataaat gcttcaataa tattgaaaaa ggaagagtat gagtattcaa   3720
catttccgtg tcgcccttat tcccttttt gcggcatttt gccttcctgt ttttgctcac   3780
ccagaaacgc tggtgaaagt aaaagatgct gaagatcagt tgggtgcacg agtgggttac   3840
atcgaactgg atctcaacag cggtaagatc cttgagagtt ttcgccccga gaacgttttt   3900
ccaatgatga gcacttttaa agttctgcta tgtggcgcgg tattatcccg tgatgacgcc   3960
gggcaagagc aactcggtcg ccgcatacac tattctcaga atgacttggt tgagtactca   4020
ccagtcacag aaaagcatct tacgatggc atgcagtaa gagaattatg cagtgctgcc    4080
ataaccatga gtgataacac tgcggccaac ttacttctga acgatcgg aggaccgaag    4140 gagctaaccg cttttttgca acatgggg atcatgtaa ctcgccttga tcgttgggaa     4200
ccggagctga atgaagccat accaaacgac gagcgtgaca ccacgatgcc agcagcaatg   4260
```

```
gcaacaacgt tgcgcaaact attaactggc gaactactta ctctagcttc ccggcaacaa    4320
ttaatagact ggatggaggc ggataaagtt gcaggaccac ttctgcgctc ggcccttccg    4380
gctggctggt ttattgctga taaatctgga gccggtgagc gtgggtctcg cggtatcatt    4440
gcagcactgg ggccagatgg taagcccctcc cgtatcgtag ttatctacac gacggggagt    4500
caggcaacta tggatgaacg aaatagacag atcgctgaga taggtgcctc actgattaag    4560
cattggtaac tgtcagacca agtttactca tatatacttt agattgattt aaaacttcat    4620
ttttaattta aaaggatcta ggtgaagatc cttttttgata atctcatgac caaaatccct    4680
taacgtgagt tttcgttcca ctgagcgtca gacccccgtag aaaagatcaa aggatcttct    4740
tgagatcctt ttttttctgcg cgtaatctgc tgcttgcaaa caaaaaaacc accgctacca    4800
gcggtggttt gtttgccgga tcaagagcta ccaactcttt ttccgaaggt aactggcttc    4860
agcagagcgc agataccaaa tactgtcctt ctagtgtagc cgtagttagg ccaccacttc    4920
aagaactctg tagcaccgcc tacatacctc gctctgctaa tcctgttacc agtggctgct    4980
gccagtggcg ataagtcgtg tcttaccggg ttggactcaa gacgatagtt accggataag    5040
gcgcagcggt cgggctgaac ggggggttcg tgcacacagc ccagcttgga gcgaacgacc    5100
tacaccgaac tgagatacct acagcgtgag cattgagaaa cgccacgct tcccgaaggg    5160 agaaaggcgg acaggtatcc ggtaagcggc agggtcggaa caggagagcg cacgagggag    5220
cttccagggg gaaacgcctg gtatctttat agtcctgtcg ggtttcgcca cctctgactt    5280
gagcgtcgat ttttgtgatg ctcgtcaggg gggcggagcc tatggaaaaa cgccagcaac    5340
gcggcctttt tacggttcct ggccttttgc tggccttttg ctcacatgtt ctttcctgcg    5400
ttatcccctg attctgtgga taaccgtatt accgcctttg agtgagctga taccgctcgc    5460
cgcagccgaa cgaccgagcg cagcgagtca gtgagcgagg aagcggaaga gcgcccaata    5520
cgcaaaccgc ctctccccgc gcgttggccg attcattaat ccagctggca cgacaggttt    5580
cccgactgga aagcgggcag tgagcgcaac gcaattaatg tgagttacct cactcattag    5640
gcaccccagg ctttacactt tatgcttccg gctcgtatgt tgtgtggaat tgtgagcgga    5700
taacaatttc acacaggaaa cagctatgac catgattacg aatta               5746
```

<210> SEQ ID NO 45
<211> LENGTH: 286
<212> TYPE: PRT
<213> ORGANISM: Homo sapiens

<400> SEQUENCE: 45

```
Met Ser Ile Gln His Phe Arg Val Ala Leu Ile Pro Phe Phe Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Asp Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110
```

Asp Gly Met Thr Val Arg Glu Leu Cys Ser Ala Ala Ile Thr Met Ser
            115                 120                 125

Asp Asn Thr Ala Ala Asn Leu Leu Leu Thr Thr Ile Gly Gly Pro Lys
        130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 46
<211> LENGTH: 5074
<212> TYPE: DNA
<213> ORGANISM: Homo sapiens

<400> SEQUENCE: 46

| | | |
|---|---|---|
| ttcgagctcg cccgacattg attattgact agttattaat agtaatcaat tacggggtca | 60 |
| ttagttcata gcccatatat ggagttccgc gttacataac ttacggtaaa tggcccgcct | 120 |
| ggctgaccgc ccaacgaccc ccgcccattg acgtcaataa tgacgtatgt tcccatagta | 180 |
| acgccaatag ggactttcca ttgacgtcaa tgggtggagt atttacgtaa aactgcccac | 240 |
| ttggcagtac atcaagtgta tcatatgcca agtacgcccc ctattgacgt caatgacggt | 300 |
| aaatggcccg cctggcatta tgcccagtac atgaccttat gggactttcc tacttggcag | 360 |
| tacatctacg tattagtcat cgctattacc atggtgatgc ggttttggca gtacatcaat | 420 |
| gggcgtggat agcggtttga ctcacgggga tttccaagtc tccaccccat tgacgtcaat | 480 |
| gggagtttgt tttggcacca aaatcaacgg gactttccaa aatgtcgtaa caactccgcc | 540 |
| ccattgacgc aaatgggcgg taggcgtgta cggtgggagg tctatataag cagagctcgt | 600 |
| ttagtgaacc gtcagatcgc ctggagacgc catccacgct gttttgacct ccatagaaga | 660 |
| caccgggacc gatccagcct ccgcggccgg gaacggtgca ttggaacgcg gattccccgt | 720 |
| gccaagagtg acgtaagtac cgcctataga gtctataggc ccaccccctt ggcttcgtta | 780 |
| gaacgcggct acaattaata cataacctta tgtatcatac atacgattt aggtgacac | 840 |
| tatagaataa catccacttt gcctttctct ccacaggtgt ccactcccag gtccaactgc | 900 |
| acctcggttc tatcgattga attccaccat gggatggtca tgtatcatcc ttttttctagt | 960 |
| agcaactgca accggtgtac actcgagcgt acggtggctg caccatctgt cttcatcttc | 1020 |
| ccgccatctg atgagcagtt gaaatctgga actgcctctg ttgtgtgcct gctgaataac | 1080 |
| ttctatccca gagaggccaa agtacagtgg aaggtggata acgccctcca atcgggtaac | 1140 |

-continued

| | |
|---|---|
| tcccaggaga gtgtcacaga gcaggacagc aaggacagca cctacagcct cagcagcacc | 1200 |
| ctgacgctga gcaaagcaga ctacgagaaa cacaaagtct acgcctgcga agtcacccat | 1260 |
| cagggcctga gctcgcccgt cacaaagagc ttcaacaggg gagagtgtta aagcttggc | 1320 |
| cgccatggcc caacttgttt attgcagctt ataatggtta caaataaagc aatagcatca | 1380 |
| caaatttcac aaataaagca ttttttttcac tgcattctag ttgtggtttg tccaaactca | 1440 |
| tcaatgtatc ttatcatgtc tggatcgatc gggaattaat tcggcgcagc accatggcct | 1500 |
| gaaataacct ctgaaagagg aacttggtta ggtaccttct gaggcggaaa gaaccagctg | 1560 |
| tggaatgtgt gtcagttagg gtgtggaaag tccccaggct ccccagcagg cagaagtatg | 1620 |
| caaagcatgc atctcaatta gtcagcaacc aggtgtggaa agtccccagg ctccccagca | 1680 |
| ggcagaagta tgcaaagcat gcatctcaat tagtcagcaa ccatagtccc gcccctaact | 1740 |
| ccgcccatcc cgcccctaac tccgcccagt tccgcccatt ctccgcccca tggctgacta | 1800 |
| atttttttta tttatgcaga ggccgaggcc gcctcggcct ctgagctatt ccagaagtag | 1860 |
| tgaggaggct ttttttggagg cctaggcttt tgcaaaaagc tgttaacagc ttggcactgg | 1920 |
| ccgtcgtttt acaacgtcgt gactgggaaa accctggcgt tacccaactt aatcgccttg | 1980 |
| cagcacatcc cccttcgcc agctggcgta atagcgaaga ggcccgcacc gatcgccctt | 2040 |
| cccaacagtt gcgtagcctg aatggcgaat ggcgcctgat gcggtatttt ctccttacgc | 2100 |
| atctgtgcgg tatttcacac cgcatacgtc aaagcaacca tagtacgcgc cctgtagcgg | 2160 |
| cgcattaagc gcggcgggtg tggtggttac gcgcagcgtg accgctacac ttgccagcgc | 2220 |
| cctagcgccc gctcctttcg ctttcttccc ttcctttctc gccacgttcg ccggctttcc | 2280 |
| ccgtcaagct ctaaatcggg ggctcccttt agggttccga tttagtgctt tacggcacct | 2340 |
| cgaccccaaa aaacttgatt tgggtgatgg ttcacgtagt gggccatcgc cctgatagac | 2400 |
| ggttttttcgc cctttgacgt tggagtccac gttctttaat agtggactct tgttccaaac | 2460 |
| tggaacaaca ctcaaccta tctcgggcta ttcttttgat ttataaggga ttttgccgat | 2520 |
| ttcggcctat tggttaaaaa atgagctgat ttaacaaaaa tttaacgcga attttaacaa | 2580 |
| aatattaacg tttacaattt tatggtgcac tctcagtaca atctgctctg atgccgcata | 2640 |
| gttaagccaa ctccgctatc gctacgtgac tgggtcatgg ctgcgccccg acacccgcca | 2700 |
| acacccgctg acgcgccctg acgggcttgt ctgctcccgg catccgctta cagacaagct | 2760 |
| gtgaccgtct ccgggagctg catgtgtcag aggttttcac cgtcatcacc gaaacgcgcg | 2820 |
| aggcagtatt cttgaagacg aaagggcctc gtgatacgcc tatttttata ggttaatgtc | 2880 |
| atgataataa tggtttctta gacgtcaggt ggcactttc ggggaaatgt gcgcggaacc | 2940 |
| cctatttgtt tatttttcta aatacattca aatatgtatc cgctcatgag acaataaccc | 3000 |
| tgataaatgc ttcaataata ttgaaaaagg aagagtatga gtattcaaca tttccgtgtc | 3060 |
| gcccttattc ccttttttgc ggcattttgc cttcctgttt ttgctcaccc agaaacgctg | 3120 |
| gtgaaagtaa aagatgctga agatcagttg ggtgcacgag tgggttacat cgaactggat | 3180 |
| ctcaacagcg gtaagatcct tgagagtttt cgccccgaag aacgttttcc aatgatgagc | 3240 |
| acttttaaag ttctgctatg tggcgcggta ttatcccgtg atgacgccgg caagagcaa | 3300 |
| ctcggtcgcc gcatacacta ttctcagaat gacttggttg agtactcacc agtcacagaa | 3360 |
| aagcatctta cggatggcat gacagtaaga gaattatgca gtgctgccat aaccatgagt | 3420 |
| gataacactg cggccaactt acttctgaca acgatcggag gaccgaagga gctaaccgct | 3480 |
| tttttgcaca acatggggga tcatgtaact cgccttgatc gttgggaacc ggagctgaat | 3540 |

-continued

```
gaagccatac caaacgacga gcgtgacacc acgatgccag cagcaatggc aacaacgttg    3600
cgcaaactat taactggcga actacttact ctagcttccc ggcaacaatt aatagactgg    3660
atggaggcgg ataaagttgc aggaccactt ctgcgctcgg cccttccggc tggctggttt    3720
attgctgata aatctggagc cggtgagcgt gggtctcgcg gtatcattgc agcactgggg    3780
ccagatggta agccctcccg tatcgtagtt atctacacga cggggagtca ggcaactatg    3840
gatgaacgaa atagacagat cgctgagata ggtgcctcac tgattaagca ttggtaactg    3900
tcagaccaag tttactcata tatactttag attgatttaa aacttcattt ttaatttaaa    3960
aggatctagg tgaagatcct ttttgataat ctcatgacca aaatcccttg acgtgagttt    4020
tcgttccact gagcgtcaga ccccgtagaa aagatcaaag gatcttcttg agatcctttt    4080
tttctgcgcg taatctgctg cttgcaaaca aaaaaaccac cgctaccagc ggtggtttgt    4140
ttgccggatc aagagctacc aactcttttt ccgaaggtaa ctggcttcag cagagcgcag    4200
ataccaaata ctgtccttct agtgtagccg tagttaggcc accacttcaa gaactctgta    4260
gcaccgccta catacctcgc tctgctaatc ctgttaccag tggctgctgc cagtggcgat    4320
aagtcgtgtc ttaccgggtt ggactcaaga cgatagttac cggataaggc gcagcggtcg    4380
ggctgaacgg ggggttcgtg cacacagccc agcttggagc gaacgaccta caccgaactg    4440
agatacctac agcgtgagca ttgagaaagc gccacgcttc ccgaagggag aaaggcggac    4500
aggtatccgg taagcggcag ggtcggaaca ggagagcgca cgagggagct tccaggggga    4560
aacgcctggt atctttatag tcctgtcggg tttcgccacc tctgacttga gcgtcgattt    4620
ttgtgatgct cgtcaggggg gcggagccta tggaaaaacg ccagcaacgc ggccttttta    4680
cggttcctgg ccttttgctg gccttttgct cacatgttct ttcctgcgtt atccctgat     4740
tctgtggata accgtattac cgcctttgag tgagctgata ccgctcgccg cagccgaacg    4800
accgagcgca gcgagtcagt gagcgaggaa gcggaagagc gcccaatacg caaaccgcct    4860
ctccccgcgc gttggccgat tcattaatcc agctggcacg acaggtttcc cgactggaaa    4920
gcgggcagtg agcgcaacgc aattaatgtg agttacctca ctcattaggc acccaggct     4980
ttacacttta tgcttccggc tcgtatgttg tgtggaattg tgagcggata acaatttcac    5040
acaggaaaca gctatgacca tgattacgaa ttaa                                5074
```